United States Patent [19]

Hudspeth et al.

[11] Patent Number: 4,895,834

[45] Date of Patent: * Jan. 23, 1990

[54] RENIN INHIBITORS III

[75] Inventors: James P. Hudspeth, Malibu, Calif.; James S. Kaltenbronn, Ann Arbor, Mich.; Joseph T. Repine, Ann Arbor, Mich.; William H. Roark, Ann Arbor, Mich.; Michael A. Stier, Ann Arbor, Mich.

[73] Assignee: Warner-Lambert Company, Morris Plains, N.J.

[*] Notice: The portion of the term of this patent subsequent to Apr. 5, 2005 has been disclaimed.

[21] Appl. No.: 113,277

[22] Filed: Nov. 2, 1987

Related U.S. Application Data

[63] Continuation-in-part of Ser. No. 941,966, Jan. 15, 1986, Pat. No. 4,735,933.

[51] Int. Cl.[4] .................... H61K 37/02; C07K 5/06; C07K 5/08
[52] U.S. Cl. ......................... 514/18; 514/19; 530/330; 530/331; 546/205; 546/210; 546/223; 546/233; 546/276; 546/335; 546/336; 548/344; 560/41; 562/450
[58] Field of Search ............... 514/18, 19; 530/330, 530/331; 546/205, 210, 223, 233, 278, 335, 336; 548/344; 560/41; 562/450

[56] References Cited

U.S. PATENT DOCUMENTS 4,735,933  4/1988  Hudspeth et al. ............... 514/18

Primary Examiner—Lester L. Lee
Attorney, Agent, or Firm—Elizabeth M. Anderson

[57] ABSTRACT

The invention concerns novel renin-inhibitory peptides which are useful for treating renin associated hypertension, hyperaldosternoism, and congestive heart failure. Processes for preparing the peptides, compositions containing them and methods of using them are included. Also included is a diagnostic test using the compounds to determine the presence of renin-associated hypertension or hyperaldosteronism.

10 Claims, No Drawings

RENIN INHIBITORS III

CROSS-REFERENCE

This application is a continuation-in-part of copending application Ser. No. 941,966 filed Dec. 15, 1986, now U.S. Pat. No. 4,735,933.

BACKGROUND OF THE INVENTION

Renin is a natural enzyme which is released into the blood from the kidney. It cleaves its natural substrate, angiotensinogen, releasing decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renins have been sought as an agent for control of hypertension and hyperaldosteronism.

The present invention concerns novel peptides which inhibit renin. It also concerns pharmaceutical compositions containing these novel peptides, methods of treating renin-associated hypertension, hyperaldosteronism, and congestive heart failure, as well as the use of the peptides as diagnostic tools, and the methods for preparing the peptides.

U.S. Pat. No. 4,479,941 covers certain renin-inhibitory peptides of the formula $$A-B-B-D-N(H)-C(R^2CH_2)(H)-C(=O)-N(O^-)-C(CH_2R^1)(H)-C(=O)-N(H)-C(R^3CH_2)(H)-C(OH)(H)-C(=O)-N(H)-C(R^4)(H)-C(=O)-E$$

European Application No. 85/308759 covers certain renin-inhibitory dipeptides of the formula $$R^1-(O)_m-CH(R^2)-C(=O)-NH-CH(R^3)-C(=O)-NH-CH(R^4)-CH(OH)-CH_2-C(=O)-R^5$$

wherein m is 0 or 1 and $R^1-R^5$ are a variety of organic groups.

European Application No. 184,855 covers renin-inhibitory peptides of the formula $$A-N(H)-C(R_1)(H)-C(=O)-N(R_2)-C(R_3)(H)-C(=O)-N(R_4)-C(R_5)(H)-CH(OH)-C(R_6)(H)-C(=O)-N(R_9)-C(R_7)(H)-X$$

wherein A is an N-protecting group; $R_1$, $R_3$, $R_5$ and $R_7$ are lower alkyl or lipophilic or aromatic amino acid side chains and may be the same or different; $R_2$, $R_4$ and $R_6$ are hydrogen or lower alkyl and may be the same or different; X is hydrogen, lower alkyl or $-CH_2-OR_8$, wherein $R_8$ is hydrogen, lower alkyl or alkaryl; and $R_9$ is lower alkyl, hydroxy, hydroxyalkyl, alkoxy, allyl, alkaryloxy or thioalkyl and pharmaceutically acceptable salts thereof.

SUMMARY OF THE INVENTION

The present invention relates to novel peptides of the formula $$ACYL-X-Y-W-U \qquad (I)$$

and the pharmaceutically acceptable acid addition salts thereof wherein ACYL, X, Y, W, and U are as defined herein below.

The invention also includes pharmaceutical compositions comprising an effective amount of the above peptie of formula I in admixture with a pharmaceutically acceptable carrier or excipient and a method for treating renin-associated hypertension in a patient suffering therefrom comprising administering to said patient the above pharmaceutical composition in unit dosage form.

Further the invention includes a pharmaceutical composition comprising an effective amount of a peptide of formula I above in admixture with a pharmaceutically acceptable carrier or excipient, and a method for treating hyperaldosteronism in a patient suffering therefrom comprising administering to said patient the above pharmaceutical composition in unit dosage form.

The present invention also includes the use of peptides of formula I above as diagnostic tools for the identification of cases of hypertension due to renin excess.

The invention further includes methods for preparing peptides of formula I above.

Also the invention includes a pharmaceutical composition comprising an amount effective for treating congestive heart failure of a compound of formula I above in admixture with a pharmaceutically acceptable carrier or excipient and a method of treating congestive heart failure in a patient suffering therefrom comprising administering to said patient the above pharmaceutical composition in unit dosage form.

DETAILED DESCRIPTION

The following table provides a dictionary of the terms used in the description of the invention.

TABLE I

| Abbreviated Designation | Amino Acid |
|---|---|
| HIS | L-Histidine |
| D-HIS | D-Histidine |
| LEU | L-Leucine |
| D-LEU | D-Leucine |
| STA | 4(S)—Amino-3(S)—hydroxy-6-methylheptanoic acid |
| PHSTA | 4(S)—Amino-3(S)—hydroxy-5-phenylpentanoic acid |
| CYSTA | 4(S)—Amino-3(S)—hydroxy-5-cyclohexanepentanoic acid |

TABLE I-continued

| Abbreviated Designation | Amino Acid |
| --- | --- |
| ILE | L-Isoleucine |
| D-ILE | D-Isoleucine |
| N—MeHIS | N—Methylhistidine |
| N—MeLEU | N—Methylleucine |
| N—MeILE | N—Methylisoleucine |
| PHE | L-Phenylalanine |
| HOMOPHE | Homophenylalanine |
| HOMOHIS | Homohistidine |
| NLE | Norleucine |
| VAL | L-Valine |
| ASP | L-Aspartic acid |
| *Protecting Group* | |
| Z | Benzyloxycarbonyl |
| BOC | Tert-butyloxycarbonyl |
| TRT | Trityl |
| TOS | Tosyl |
| *Acyl Group* | |
| DNMA | Di-(1-naphthylmethyl)acetyl |
| *Amides With* | |
| —NHCH₂Ph | Benzylamine |
| —NHCH₂—⟨cyclohexyl⟩ | Cyclohexylmethylamine |
| —NHCH₂—⟨phenyl⟩—CH₂NHZ (BOC) | m-Xylene-di-amine (Z or BOC) |
| —NHCH₂—⟨phenyl⟩—CH₂NH₂ | m-Xylene-di-amine |
| —NH₂ | Ammonia |
| —NH—⟨piperidine⟩N—CH₂Ph | 4-Amino-N—benzylpiperidine |
| —NH—⟨piperidine⟩NH | 4-Aminopiperidine |
| —NH—CH₂—⟨pyridine⟩ | 2-Aminomethylpyridine |
| —NHCH₂CHCH₂CH₃<br>        CH₃ | 2-Methylbutylamine |
| —NHCH—CH(CH₃)CH₂CH₃<br>    CH₂OH | 1-Hydroxymethyl-2-methylbutylamine |
| *Esters With* | |
| —OCH₃ | Methanol |
| —OC₂H₅ | Ethanol |

The peptides of the present invention are represented by the formula $$\text{ACYL—X—Y—W—U} \qquad \text{I}$$

and the pharmaceutically acceptable acid addition salts thereof, wherein ACYL is DNMA,

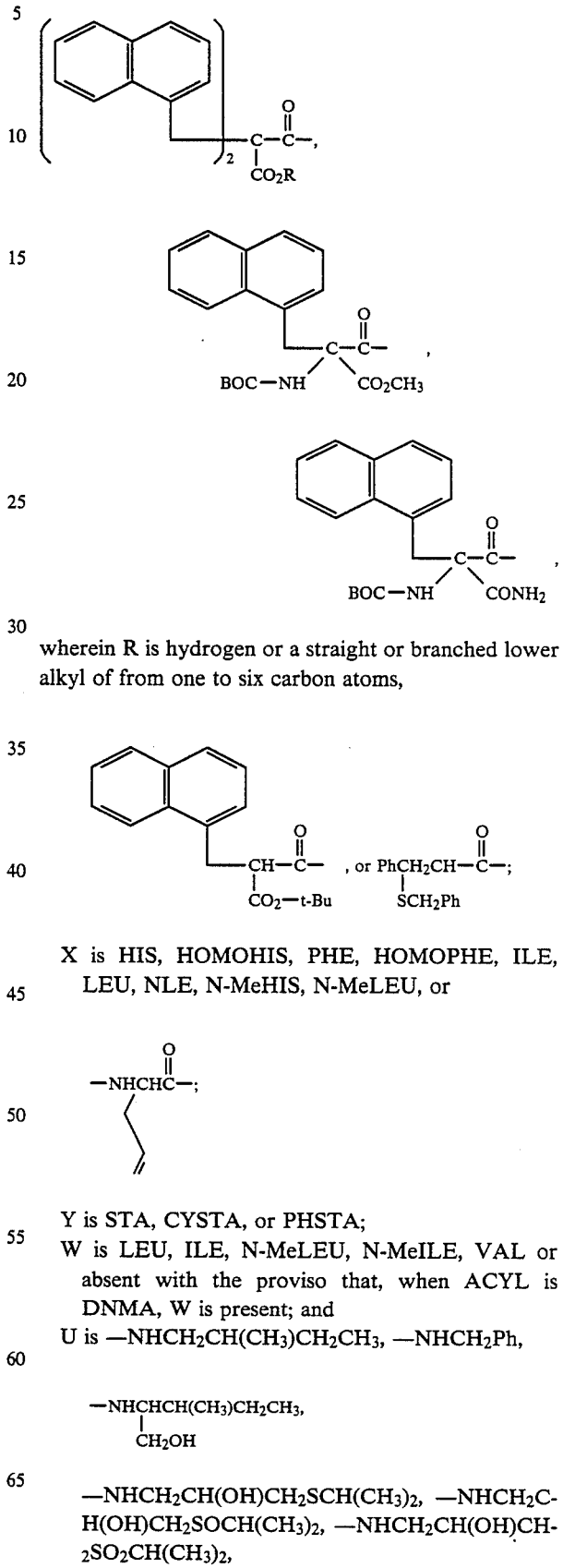

wherein R is hydrogen or a straight or branched lower alkyl of from one to six carbon atoms, X is HIS, HOMOHIS, PHE, HOMOPHE, ILE, LEU, NLE, N-MeHIS, N-MeLEU, or $$-\text{NHCHC}-\overset{\text{O}}{\underset{\|}{\text{C}}}-;$$

Y is STA, CYSTA, or PHSTA;

W is LEU, ILE, N-MeLEU, N-MeILE, VAL or absent with the proviso that, when ACYL is DNMA, W is present; and U is —NHCH₂CH(CH₃)CH₂CH₃, —NHCH₂Ph,

—NHCHCH(CH₃)CH₂CH₃,
    CH₂OH

—NHCH₂CH(OH)CH₂SCH(CH₃)₂, —NHCH₂CH(OH)CH₂SOCH(CH₃)₂, —NHCH₂CH(OH)CH₂SO₂CH(CH₃)₂,

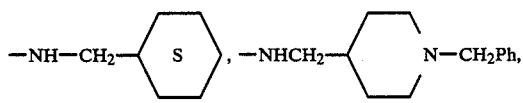

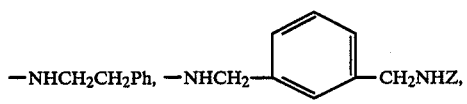

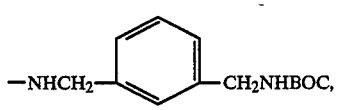

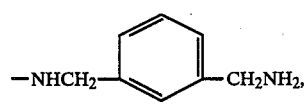

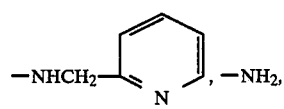, —NHCH₂CH=CH₂, —OC₂H₅, —OCH₃, or

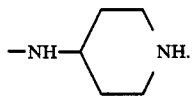

Preferred compounds of the present invention are compounds of formula I wherein U is
—NHCH₂Ph,

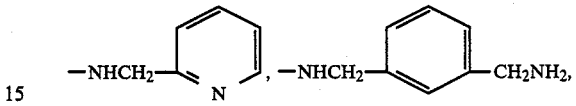

—NHCH₂CH=CH₂, —NHCH₂CH(OH)CH₂SCH(CH₃)₂,
—NHCH₂CH(OH)CH₂SOCH(CH₃)₂,
—NHCH₂CH(OH)CH₂SO₂CH(CH₃)₂, or
—NHCH₂CH(CH₃)CH₂CH₃.

Particularly valuable compounds falling within the scope of the invention include the following compounds, their isomers, and pharmaceutically acceptable acid addition salts:

DNMA-HIS-STA-LEU-NHCH₂Ph,

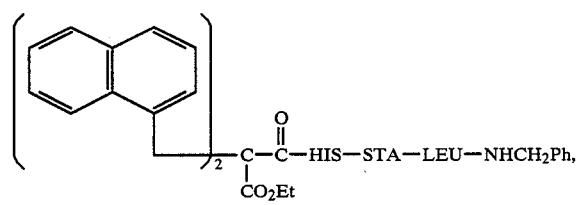

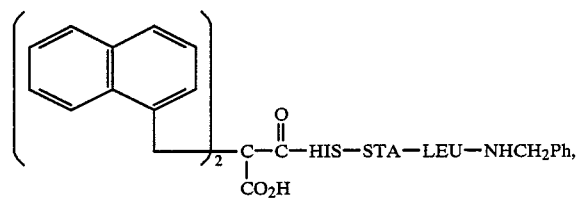

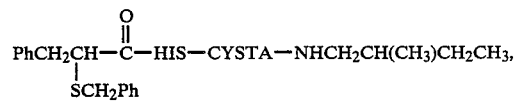

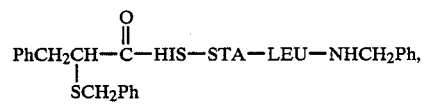

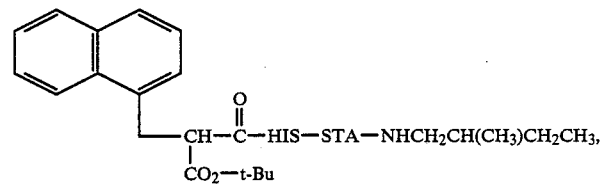

DNMA—HIS—STA—NHCH₂CH=CH₂,
DNMA—HIS—STA—NHCH₂CH(OH)CH₂SCH(CH₃)₂,
DNMA—HIS—STA—NHCH₂CH(OH)CH₂SO₂CH(CH₃)₂,

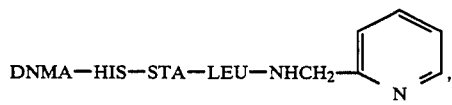
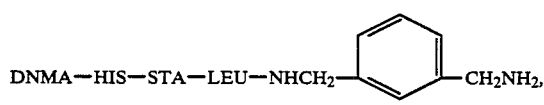
DNMA-(D-HIS)-STA-LEU-NHCH2Ph,
DNMA-HIS-STA-(D-LEU)-NHCH2Ph,
DNMA-(N-MeHIS)-STA-LEU-NHCH2Ph,
DNMA-HIS-STA-(N-MeLEU)-NHCH2Ph,
DNMA-HIS-CYSTA-LEU-NHCH2Ph,
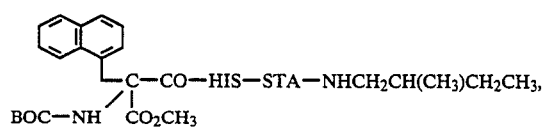
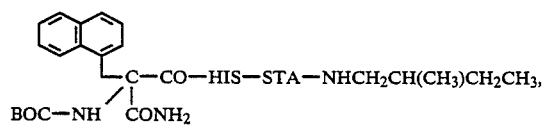
DNMA-ASP(OCH2Ph)-CYSTA-LEU-NHCH2Ph,
DNMA-ASP-CYSTA-LEU-NHCH2Ph,
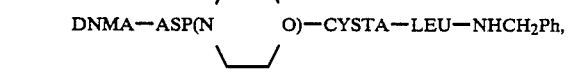
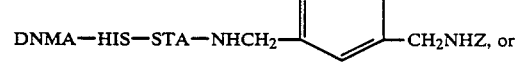
Other compounds of the present invention include the following:
DNMA-HIS-STA-ILE-NHCH2Ph,
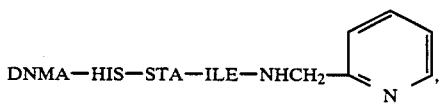
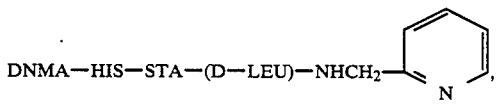
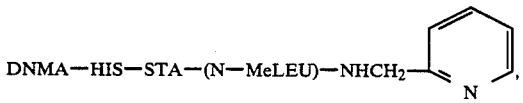
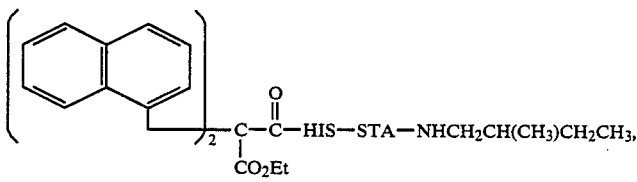

-continued
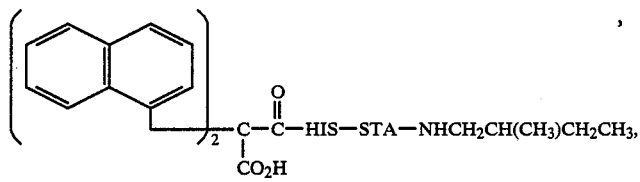
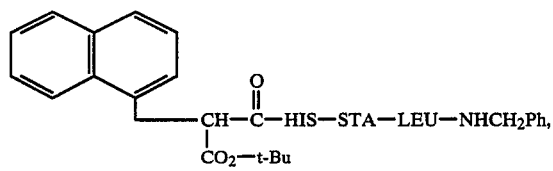
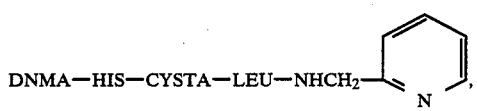
DNMA-LEU-STA-LEU-NHCH₂Ph,
DNMA-ILE-STA-LEU-NHCH₂Ph,
DNMA-LEU-CYSTA-LEU-NHCH₂Ph,
DNMA-LEU-CYSTA-ILE-NHCH₂Ph,
DNMA-HIS-CYSTA-ILE-NHCH₂Ph,
DNMA-PHE-STA-LEU-NHCH₂Ph,
DNMA-HOMOHIS-CYSTA-LEU-NHCH₂Ph,
DNMA-NLE-STA-LEU-NHCH₂Ph,
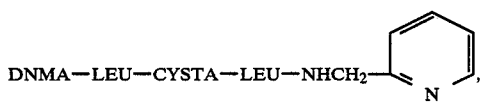
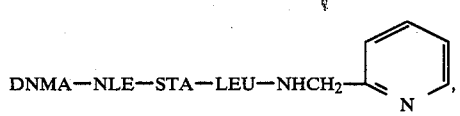
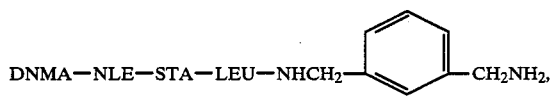
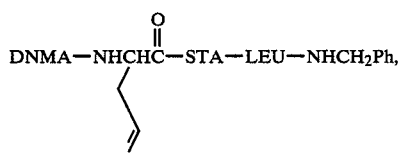
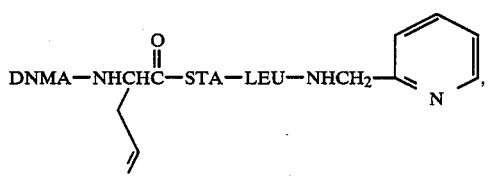

-continued
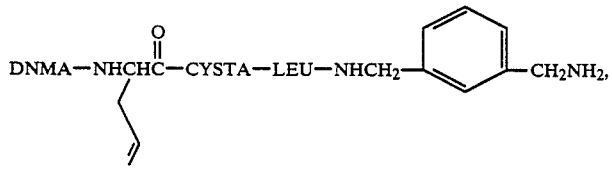
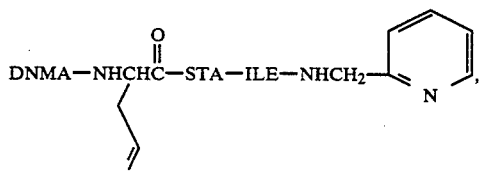
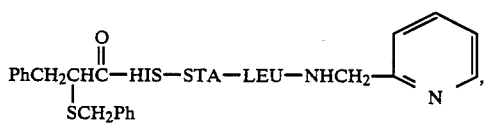
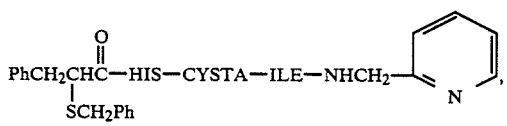
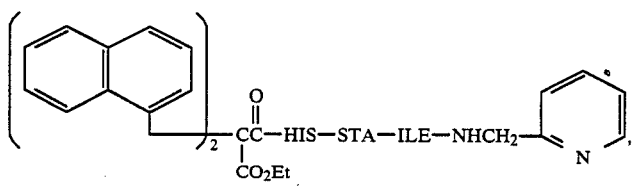
DNMA—(N—MeLEU)—STA—LEU—NHCH$_2$Ph,
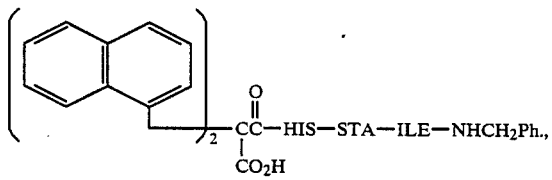
DNMA—HIS—PHSTA—LEU—NHCH$_2$Ph,
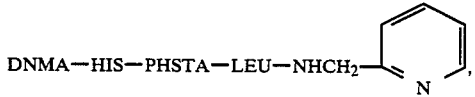
DNMA-LEU-STA-NHCH$_2$CH(OH)CH$_2$SCH(CH$_3$)$_2$,
DNMA-LEU-STA-NHCH$_2$CH(OH)CH$_2$SOCH(CH$_3$)$_2$,
DNMA-LEU-STA-NHCH$_2$CH(OH)CH$_2$SO$_2$CH(CH$_3$)$_2$,
DNMA-HIS-STA-NHCH$_2$CH(OH)CH$_2$SOCH(CH$_3$)$_2$,
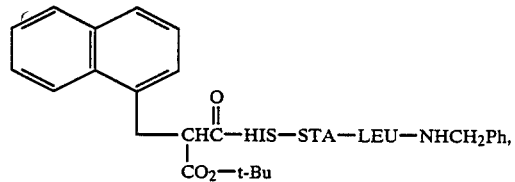

-continued
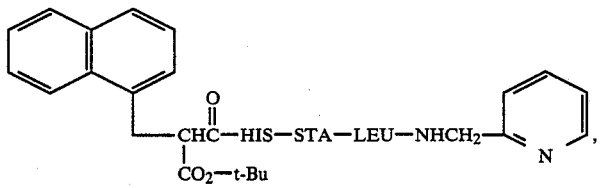
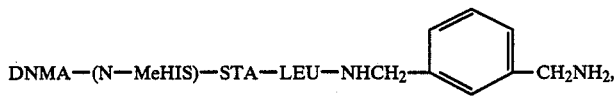
DNMA—(N—MeHIS)—CYSTA—LEU—NHCH₂Ph,
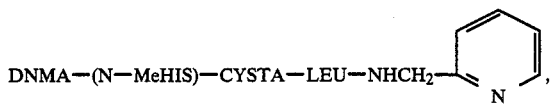
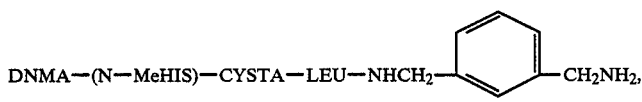
DNMA—HIS—STA—(N—MeILE)—NHCH₂Ph,
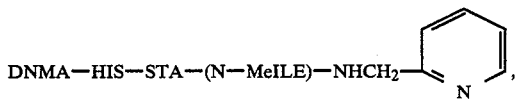
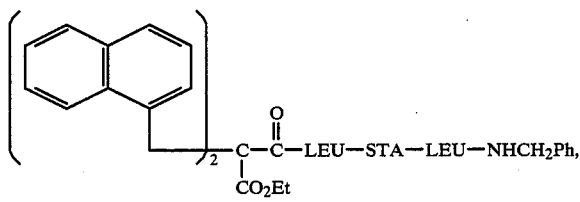
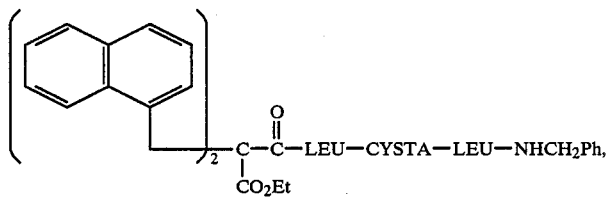
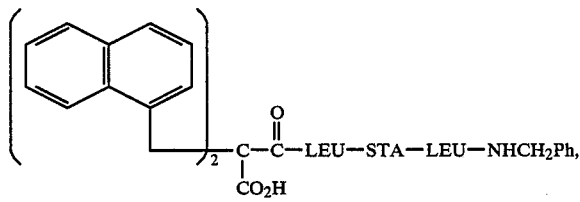
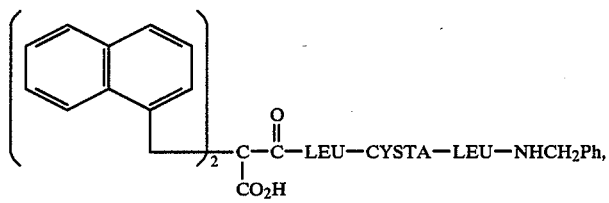

DNMA—HIS—STA—LEU—NHCH2CH=CH2,
DNMA—HIS—CYSTA—LEU—NHCH2CH=CH2,
DNMA—HIS—STA—ILE—NHCH2CH=CH2,

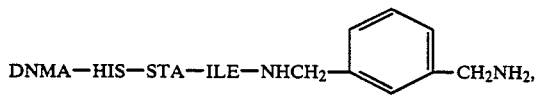

DNMA—HIS—STA—VAL—NHCH2Ph,

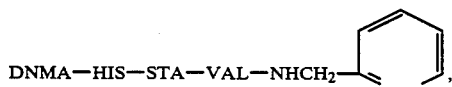

DNMA-HIS-STA-(D-ILE)-NHCH2Ph, and
DNMA-HOMOPHE-STA-LEU-NHCH2Ph.

The compounds of the present invention include solvates, hydrates and pharmaceutically acceptable acid addition salts of the basic compounds of formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic and the like. The salts are prepared by contacting the free base form with a sufficient amount of the desired acid to produce a salt in the conventional manner. The free base forms may be regenerated by treating the salt form with a base.

The modified peptides of the present invention possess one or more chiral centers and each center may exist in the R(D) or S(L) configuration. The present invention includes all enantiomeric and epimeric forms as well as the appropriate mixtures thereof.

Some of the above novel peptides may be prepared in accordance with well-known procedures for preparing peptides from their constituent amino acids. Other of the novel peptides of the present invention are prepared by a step-wise procedure or by a fragment coupling procedure depending upon the particular final product desired.

The following schemes illustrate novel methods of preparing certain peptides of the present invention.

According to Scheme I above, a BOC-protected, NH-substituted-1-alkene (1), for example, an allyl amine is reacted with an epoxidizing agent to form the corresponding protected epoxide (2). The epoxide is reacted with a mercaptan forming a protected thioether (3). The thioether is then reacted with HCl to remove the protecting group forming the corresponding compound (4) with a free amino terminus. The amine is reacted with an amino acid or a peptide, having a free terminal carboxylic acid, for example, DNMA-HIS(TRT)-STA, to form the corresponding peptide having a thio-containing amide moiety (5) which is then reacted with aqueous acetic acid to remove the TRT group forming the desired compound (6), of formula I of the instant invention. This may be converted, if desired, to a pharmaceutically acceptable acid addition salt.

Epoxidizing agents useful in the reaction are m-chloroperbenzoic acid, perbenzoic acid, and perphthalic acid. The preferred agent is m-chloroperbenzoic acid.

The reaction takes place in an inert solvent such as methylene chloride, tetrahydrofuran, chloroform, dioxane, or ethyl acetate. The preferred solvent is methylene chloride.

Among the mercaptans possible in this sequence are any of the alkyl mercaptans, aralkyl mercaptans, or aryl mercaptans. The preferred mercaptan is isopropyl mercaptan.

The protecting group is removed with a strong acid such as trifluoroacetic, HCl, or HBr. Preferably HCl is used.

Removal of TRT is accomplished with aqueous acetic acid, dilute HCl, or dilute H2SO4. Preferably this is done with aqueous acetic acid.

The epoxidation reaction is mildly exothermic and can be carried out at temperatures between 0° and 25° C. The preferred reaction temperature is about room temperature.

The reaction time varies from 4 to 48 hours. Preferably it is about 24 hours.

The term protecting group refers to those groups intended to protect the N-terminus against undesirable reactions during synthetic procedures or to increase the solubility of the desired final compounds and includes but is not limited to Z and BOC.

The term lower alkyl refers to straight or branched chain alkyl radicals containing from 1 to 6 carbon atoms including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

SCHEME I

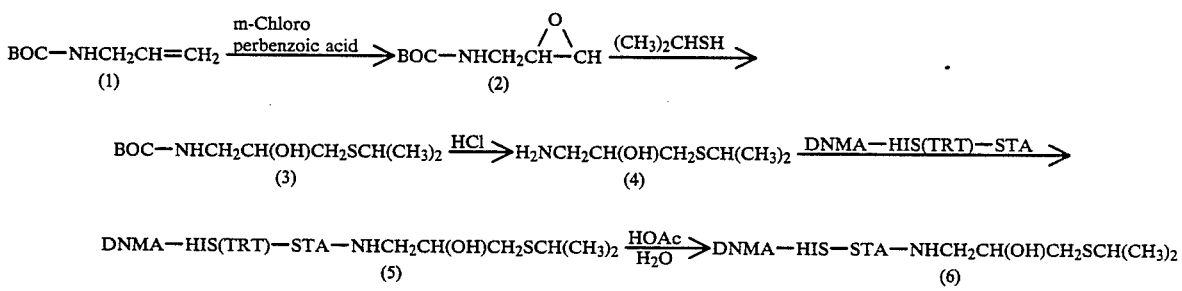

SCHEME II

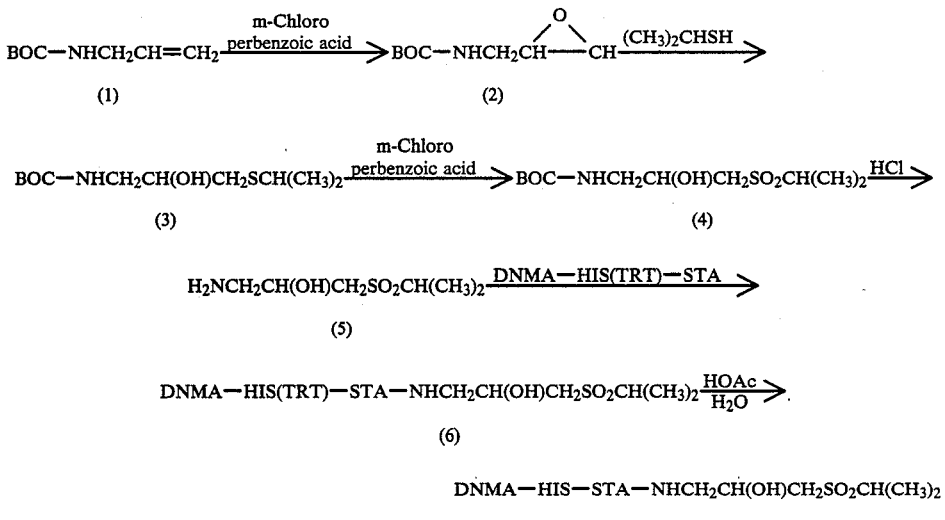

Alternatively certain compounds of the present invention having a sulfone linkage can be made according to Scheme II above. The thioether (3) of Scheme I is oxidized to form the corresponding sulfone by reaction with a peracid. The protected sulfones of (4) above are reacted with HCl to produce compounds with the free amino terminus (5). These compounds are reacted with DNMA-HIS(TRT)-STA to form a sulfone-containing peptide (6). This is reacted with aqueous acetic acid to form peptides (7) of formula I of the instant invention. These can be converted to the pharmaceutically acceptable acid addition salt.

The strategy of peptide chain assembly and selection and removal of protecting groups is discussed in Chapter 1, "The Peptide Bond," in "The Peptides. Analysis, Synthesis, Biology," E. Gross and J. Meienhofer, Eds., Academic Press, New York, NY, 1979, Vol. 1, pp. 42–44.

The DCC/HOBT method of coupling is well known to those skilled in the art and is discussed in Chapter 5, "The Carbodiimide Method" by D. H. Rich and J. Singh in "The Peptides. Analysis, Synthesis, Biology," E. Gross and J. Meienhofer, Eds., Academic Press, New York, NY, 1979, Vol. 1, pp. 241–261.

Peptide coupling depends on activating the carboxyl group of the protected amino acid prior to condensing it with another peptide containing a free amino terminus. In addition to the DCC coupling method described above, other methods of activating the carboxyl group of a protected amino acid include:

(1) The azide method—described in Chapter 4 of the above reference.
(2) The mixed anhydride method—described in Chapter 6 of the above reference.
(3) The active ester method—described in Chapter 3 of the above reference.

The compounds of the present invention are useful for treating renin-associated hypertension, congestive heart failure, and hyperaldosteronism. They are also useful as diagnostic tools for determining the presence of renin-associated hypertension or hyperaldosteronism.

Pharmaceutical compositions which comprise an effective amount of the compound in combination with a pharmaceutically acceptable carrier are part of the present invention. An important aspect of the present invention is a method of treating renin associated hypertension in a mammal which comprises administering a pharmaceutical composition containing an effective amount of a compound of the invention in combination with a pharmaceutically acceptable carrier to the mammal.

Another equally important aspect of the present invention is a method of treating hyperaldosteronism in a mammal which comprises administering a pharmaceutical composition containing an effective amount of a compound of the invention in combination with a pharmaceutically acceptable carrier to the mammal.

Still another important aspect of the present invention is a method of treating congestive heart failure in a mammal which comprises administering a pharmaceutical composition containing an effective amount of a compound of the invention in combination with a pharmaceutically acceptable carrier to the mammal.

The effectiveness of the aforementioned compound is determined by a test for in vitro renin inhibitory activity. This activity is determined by a standard radioimmunoassay for angiotensin I. In this assay the enzyme, renin, incubated for two hours at 37° in the presence of a substrate, angiotensinogen, generates the product, angiotensin I. Test compounds are added to the incubation mixture. Relative activity is reported as the IC$_{50}$, which is the molar concentration of test compound causing a 50% inhibition of the renin activity.

| Example | Activity IC$_{50}$ (M) |
|---|---|
| DNMA—HIS—STA—LEU—NHCH$_2$Ph | $1.3 \times 10^{-8}$ |

| Example | Activity IC$_{50}$ (M) |
|---|---|
| 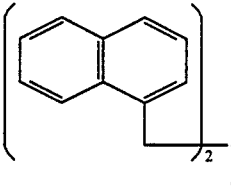 (Naphthyl-CH$_2$)$_2$C(CO$_2$Et)-CO-HIS-STA-LEU-NHCH$_2$Ph | 5.6 × 10$^{-7}$ |
| 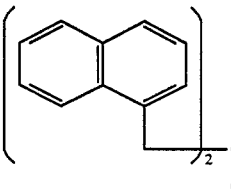 (Naphthyl-CH$_2$)$_2$C(CO$_2$H)-CO-HIS-STA-LEU-NHCH$_2$Ph | 4.3 × 10$^{-7}$ |
| 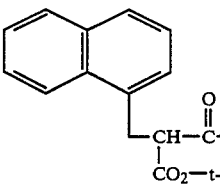 Naphthyl-CH$_2$-CH(CO$_2$-t-Bu)-CO-HIS-STA-NHCH$_2$CH(CH$_3$)CH$_2$CH$_3$ | 3.2 × 10$^{-6}$ |
| DNMA—HIS—STA—NHCH$_2$CH=CH$_2$ | 1.9 × 10$^{-7}$ |
| DNMA—HIS—STA—NHCH$_2$CH(OH)CH$_2$SCH(CH$_3$)$_2$ | 2.2 × 10$^{-7}$ |
| DNMA—HIS—STA—NHCH$_2$CH(OH)CH$_2$SO$_2$CH(CH$_3$)$_2$ | 8.2 × 10$^{-8}$ |
| 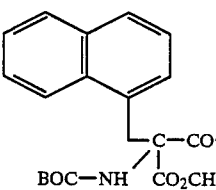 Naphthyl-CH$_2$-C(BOC-NH)(CO$_2$CH$_3$)-CO-HIS-STA-NHCH$_2$CH(CH$_3$)CH$_2$CH$_3$ | 1.5 × 10$^{-6}$ |
| 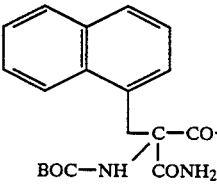 Naphthyl-CH$_2$-C(BOC-NH)(CONH$_2$)-CO-HIS-STA-NHCH$_2$CH(CH$_3$)CH$_2$CH$_3$ | 8.6 × 10$^{-7}$ |
| DNMA—HIS—STA—LEU—NHCH$_2$-C$_6$H$_4$-CH$_2$NHZ 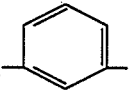 | 5.7 × 10$^{-8}$ |
| DNMA—HIS—STA—LEU—NHCH$_2$-C$_6$H$_4$-CH$_2$NH$_2$ 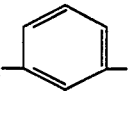 | 6.9 × 10$^{-9}$ |
| PhCH$_2$CH(SCH$_2$Ph)CO—HIS—STA—LEU—NHCH$_2$Ph | 2.2 × 10$^{-6}$ |
| PhCH$_2$CH(SCH$_2$Ph)CO—HIS—CYSTA—NHCH$_2$CH(CH$_3$)CH$_2$CH$_3$ | 1.7 × 10$^{-6}$ |

| Example | Activity IC$_{50}$ (M) |
|---|---|
| DNMA—HIS—STA—LEU—NHCH$_2$- | $2.8 \times 10^{-9}$ |
| DNMA—(D-HIS)—STA—LEU—NHCH$_2$Ph | $5.9 \times 10^{-6}$ |
| DNMA—HIS—STA—(D-LEU)—NHCH$_2$Ph | $3.2 \times 10^{-6}$ |
| DNMA—ASP(OCH$_2$Ph)—CYSTA—LEU—NHCH$_2$Ph | $4.6 \times 10^{-7}$ |
| DNMA—ASP—CYSTA—LEU—NHCH$_2$Ph | $9.8 \times 10^{-7}$ |
| DNMA—ASP(NO)—CYSTA—LEU—NHCH$_2$Ph | $1.3 \times 10^{-5}$ |
| DNMA—HIS—CYSTA—LEU—NHCH$_2$Ph | $1.2 \times 10^{-8}$ |
| DNMA—(N—MeHIS)—STA—LEU—NHCH$_2$Ph | $4.1 \times 10^{-6}$ |
| DNMA—HIS—STA—(N—MeLEU)—NHCH$_2$Ph | $3.6 \times 10^{-8}$ |
| DNMA—HIS—STA—NHCH$_2$-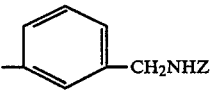-CH$_2$NHZ | $4.0 \times 10^{-6}$ |
| DNMA—HIS—STA—NHCH$_2$--CH$_2$NH$_2$ | $8.6 \times 10^{-7}$ |

The effectiveness of the aforementioned compounds in vivo is determined by their effect on lowering renin maintained blood pressure in the anesthetized, vagotomized, ganglionic-blocked rat.

After the blood pressure has stabilized, 1.25 mg/kg IV mecamylamine is added to produce ganglionic blockade. Hog renin is then infused to bring the blood pressure to a level observed before vagotomy and ganglionic blockade. Test compound is then administered IV and the drop in blood pressure is noted.

| Compound | Percent Decrease of Blood Pressure |
|---|---|
| DNMA—HIS—STA—LEU—NHCH$_2$Ph | 65% |

The compound was administered at as dose of 1 mg/kg.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents. It can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compounds of the present invention may be administered orally, buccally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerin, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 1 to 1500 mg of body weight per day or preferably 25 to 750 mg of body weight per day optionally in divided portions. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples are provided to enable one skilled in the art to practice the present invention. These examples are not intended in any way to limit the scope of the invention but are illustrative thereof.

EXAMPLE 1

DNMA-HIS-STA-LEU-NHCH$_2$Ph

DNMA-HIS(TRT)-STA-LEU-NHCH$_2$Ph (1.30 g, 1.20 mmole) was dissolved in 80 ml of 80% HOAc and heated on a steam bath for five minutes. The solution was allowed to cool to 25° over one hour, after which the solvent was removed in vacuo. The residue was dissolved in Et$_2$O to which was added brine, giving an oily preciitate of the crude product. The ether phase was separated, and the aqueous suspension of the oil was washed with ethyl ether to remove residual trityl alcohol. The aqueous and oil phases were then adjusted to pH 12 by addition of 1N NaOH, and were exhaustively extracted with EtOAc. The organic phase was washed with brine, dried over MgSO$_4$, filtered, and the filter cake washed with CH$_2$Cl$_2$. The filtrates were combined and stripped to an oil, which was taken up into a minimal amount of EtOAc. A solid was precipitated by addition of Et$_2$O, which was filtered, washed with Et$_2$O and dried to a white solid, 0.64 g. NMR, IR, and mass spectral analysis confirmed the structure of the product. Calcd. for C$_{51}$H$_{60}$N$_6$O$_5$.0.06CHCl$_3$ (MW 844.54): C, 72.62; H, 7.17; N, 9.95: Found C, 72.30; H, 7.18; N, 9.97.

EXAMPLE 2

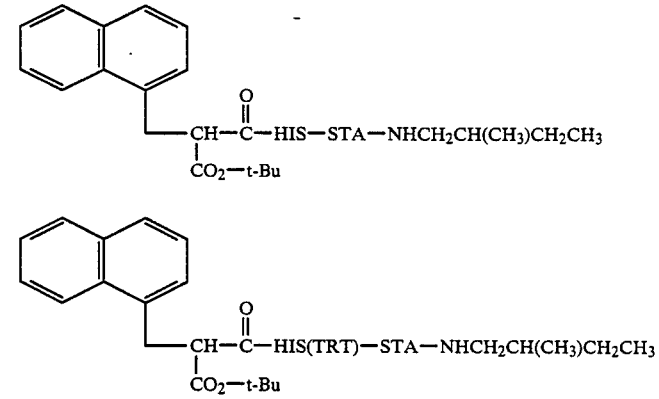

(3.53 g, 3.88 mmole) was dissolved in 25 ml of 80% HOAc and heated on a steam bath for two minutes. The solvent was removed in vacuo and the residue dissolved in EtOAc. The EtOAc solution was washed with 1 N NaOH, then brine. After drying over MgSO$_4$ and filtering, the filtrate was reduced to one-fourth volume in vacuo giving a gel. Diluting with Et$_2$O gave 2.41 g of the product as a white solid. IR, NMR, and mass spectral analysis confirmed the structure.

EXAMPLE 3

DNMA-HIS-STA-NHCH$_2$CH(OH)CH$_2$SCH(CH$_3$)$_2$

A solution of 0.5 g (0.5 mmole) of DNMA-HIS(TRT)-STA-NHCH$_2$CH(OH)CH$_2$SCH(CH$_3$)$_2$ in 15 ml of 80% HOAc was heated on a steam bath for ten minutes, then allowed to cool to room temperature. The solvent was removed in vacuo, water added, and the solution again stripped in vacuo. The residue was taken up in EtOAc, washed with brine, dried over MgSO$_4$, and filtered. Addition of Et$_2$O to the filtrate gave the crude product as a solid. Chromatography on silica gel, eluting with 2% MeOH in CHCl$_3$ gave 0.22 g of the product as a white foam. NMR and mass spectral analysis confirmed the structure.

Calcd. for C$_{44}$H$_{55}$N$_5$O$_5$S.0.16CHCl$_3$: C, 67.50; H, 7.07; N, 8.91: Found C, 67.29; H, 7.02; N, 8.83.

EXAMPLE 4

DNMA-HIS-STA-NHCH$_2$CH(OH)CH$_2$SO$_2$CH(CH$_3$)$_2$

DNMA-HIS(TRT)-STA-NHCH$_2$CH(OH)CH$_2$SO$_2$CH(CH$_3$)$_2$ (0.63 g, 0.61 mmole) was heated on a steam bath for five minutes in 15 ml 90% HOAc. After cooling to 25° over thirty minutes, the solvent was stripped off and the residue was taken up into H$_2$O. The mixture was stripped, taken up into EtOAc, and dried over MgSO$_4$. The solution was filtered and reduced in volume. Addition of Et$_2$O precipitated a solid which was collected and dried to give 0.37 g of product. NMR and mass spectral analysis confirmed the structure.

EXAMPLE 5

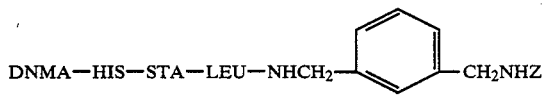

A solution of 0.5 g (0.51 mmole) of

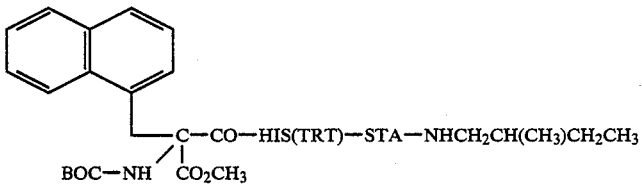

in 10 ml of 80% HOAc was heated on a steam bath for five minutes, then allowed to cool to room temperature over thirty minutes. The solvent was removed under reduced pressure and the residual oil taken up in EtOAc. The EtOAc was washed with saturated NaHCO$_3$, saturated NaCl, and dried. The EtOAc solution was concentrated to a small volume and poured into a large excess of Et$_2$O. The precipitated solid was collected and washed with Et$_2$O. There was obtained 0.22 g of the product as a white solid. The structure was confirmed by NMR and mass spectroscopy.

Calcd. for C$_{39}$H$_{56}$N$_6$O$_8$ (MW 736.92): C, 63.57; H, 7.66; N, 11.40: Found C, 63.20; H, 7.64; N, 11.10.

EXAMPLE 6

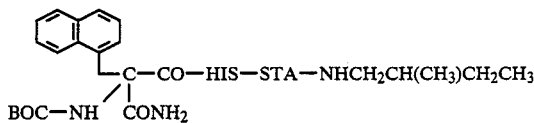

A solution of 0.22 g (0.228 mmole) of

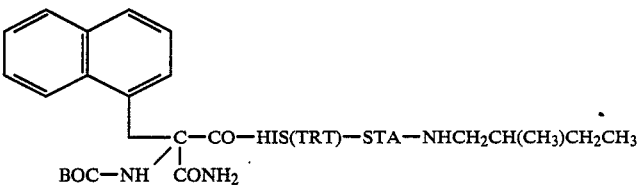

in 5 ml of 80% HOAc was heated on a steam bath for thirty minutes, the solvent then removed under reduced pressure, and the residual solid taken up in EtOAc. The solution was filtered, concentrated to a small volume under reduced pressure, and poured into excess Et$_2$O. The precipitated solid was collected and washed with Et$_2$O. There was obtained 0.08 g of the product as a white solid. The structure was confirmed by mass spectroscopy.

Calcd. for C$_{38}$H$_{55}$N$_7$O$_7$.0.75HOAc (MW 766.92): C, 61.86; H, 7.62; N, 12.78: Found C, 61.95; H, 7.63; N, 13.77.

EXAMPLE 7

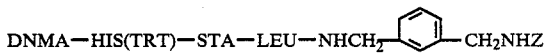

A solution of 1.80 g (1.5 mmole)

DNMA—HIS(TRT)—STA—LEU—NHCH$_2$—⟨phenyl⟩—CH$_2$NHZ in 30 ml 80% HOAc was heated on a steam bath for five minutes. After cooling to room temperature over one hour, the solution was evaporated under reduced pressure and the residue taken up in EtOAc. The solution was washed with saturated NaCl, 1N NaOH, and saturated NaCl. After drying, the solution was evaporated under reduced pressure to 15 ml in volume, and added to 200 ml of Et$_2$O. The resulting precipitate was filtered, washed with Et$_2$O, and dried to give 1.19 g of the product as a white solid. The structure was confirmed by NMR and mass spectroscopy.

Calcd. for C$_{60}$H$_{69}$N$_7$O$_7$.H$_2$O (MW 1018.28): C, 70.77; H, 7.03; N, 9.62; H$_2$O, 1.77: Found C, 71.14; H, 6.82; N, 9.61; H$_2$O, 1.79.

EXAMPLE 8

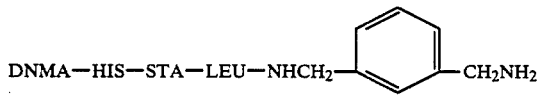

To a solution of 1.04 g (1.04 mmole) of

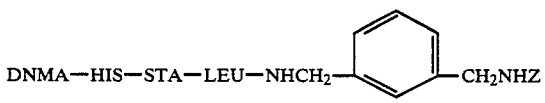

in 70 ml MeOH was added 0.15 g of 20% Pd/C catalyst. The suspension was purged with hydrogen for two and one-half hours, filtered, and evaporated under reduced pressure to give 0.87 g of a foam. The foam was triturated with Et$_2$O, filtered, and washed with Et$_2$O. There was obtained 0.84 g of product as a solid. The structure was confirmed by NMR and mass spectroscopy.

Calcd. for C$_{52}$H$_{63}$N$_7$O$_5$.H$_2$O (MW 884.14): C, 70.64; H, 7.41; N, 11.09; H$_2$O, 2.04: Found C, 70.54; H, 7.42; N, 11.07; H$_2$O, 2.10.

EXAMPLE 9

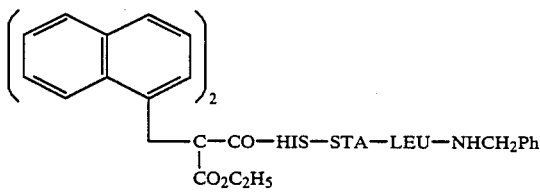

A solution of 1.03 g

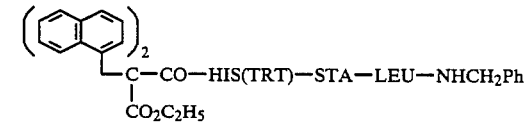

in 25 ml of 80% HOAc was heated on a steam bath for five minutes, then allowed to stand for thirty minutes at room temperature. The solvent was removed under reduced pressure and the residue triturated with H$_2$O. The residue was taken up in EtOAc and washed with saturated NaCl, saturated NaHCO$_3$, then saturated NaCl. Drying and removal of the solvent under reduced pressure left an oil. This was taken up in EtOAc and the product precipitated with Et$_2$O. There was obtained 0.5 g of the pure product as a white solid. The structure was confirmed by NMR and mass spectroscopy.

Calcd. for C$_{54}$H$_{64}$N$_6$O$_7$ (MW 909.15): C, 71.34; H, 7.09; N, 9.24: Found C, 71.34; H, 7.03; N, 9.11.

EXAMPLE 10

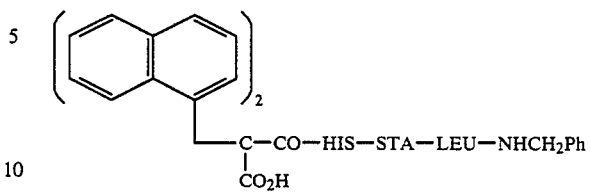

A solution of 0.58 g (0.52 mmole) of

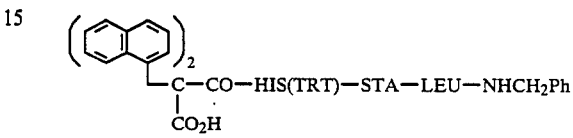

in 20 ml of 80% HOAc was heated on a steam bath for five minutes, then allowed to stand at room temperature for two hours. The mixture was filtered to remove some precipitated solid and the filtrate concentrated in vacuo. The residue was taken up in warm CHCl$_3$, washed with saturated NaCl and dried. The filtrate was concentrated and the product precipitated by the addition of Et$_2$O. There was obtained 0.36 g of product as a white solid. The structure was confirmed by NMR and mass spectroscopy.

Calcd. for C$_{52}$H$_{60}$N$_6$O$_7$.0.75H$_2$O (MW 894.56): C, 69.81; H, 6.93; N, 9.40: Found C, 69.68; H, 6.82; N, 9.41.

EXAMPLE 11

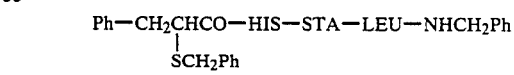

A solution of 0.22 g (0.8 mmole) of 2-benzylmercapto-3-phenylpropionic acid, 0.4 g (0.8 mmole) of HIS-STA-LEU-NHCH$_2$Ph, and 0.13 g (1.0 mmole) of HOBT in 40 ml of CH$_2$Cl$_2$/DMF (50/30) was cooled in ice and 0.16 g (0.8 mmole) of DCC added. The mixture was stirred for two days at room temperature. The mixture was filtered and diluted with EtOAc, washed with 1N citric acid then Na$_2$CO$_3$ solution, and then dried. Removal of the solvent under reduced pressure gave the crude product as a solid. Trituration with EtOAc gave 0.35 g of the pure product. The structure was confirmed by NMR and mass spectroscopy.

Calcd. for C$_{43}$H$_{56}$N$_6$O$_5$S (MW 769.02): C, 67.16; H, 7.34; N, 10.93: Found C, 66.80; H, 7.60; N, 10.85.

EXAMPLE 12

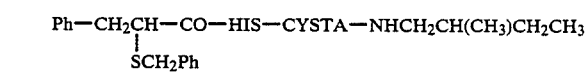

A solution of 0.47 g (0.5 mmole) of

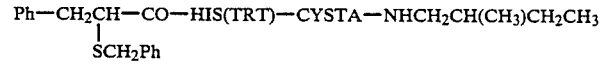

in 35 ml of 80% HOAc was heated on a steam bath for seven minutes then allowed to cool to room temperature over one hour. The solvent was removed under reduced pressure and the residue taken up in EtOAc. The EtOAc was washed with saturated NaHCO3 then saturated NaCl. Drying and removal of the solvent under reduced pressure gave the crude product. Chromatograph on silica gel, eluting with CHCl3/MeOH (95/5), gave 0.22 g of product. The structure was confirmed by mass spectroscopy.

Calcd. for $C_{38}H_{53}N_5O_4S \cdot 0.12CHCl_3$ (MW 690.17): C, 66.33; H, 7.76; N, 10.15: Found C, 66.09; H, 7.86; N, 9.88.

EXAMPLE 13

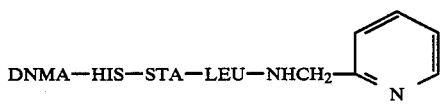

A solution of 2.0 g (1.85 mmole)

in 15 ml 80% HOAc was heated on a steam bath for seven minutes and allowed to cool to room temperature over thirty minutes. The solvent was removed under reduced pressure and the residue was taken up in EtOAc. The solution was washed with 1N NaOH and saturated NaCl, followed by drying and evaporation to 10 ml in volume under reduced pressure. This was added with rapid stirring to Et2O giving a precipitate which was filtered, washed with Et2O, and dried. There was obtained 1.2 g of the product as a white solid. The structure was confirmed by NMR and mass spectroscopy.

Calcd. for $C_{50}H_{59}N_7O_5 \cdot 0.5H_2O$ (MW 847.04): C, 70.89; H, 7.14; N, 11.57; H2O, 1.06: Found C, 71.16; H, 7.04; N, 11.62; H2O, 1.34.

EXAMPLE 14

DNMA-(D-HIS)-STA-LEU-NHCH2Ph

A solution of 0.38 g (0.38 mmole) of DNMA-(D-HIS)(TOS)-STA-LEU-NHCH2Ph in 25 ml MeOH was treated with 0.3 g (1.9 mmole) of HOBT and stirred at room temperature for fifteen hours. An additional 0.3 g (1.9 mmole) of HOBT was then added and the solution stirred an additional six hours. The solvent was removed under reduced pressure and the residue suspended in CH2Cl2. The CH2Cl2 was washed twice with saturated Na2CO3, then saturated NaCl. Drying and removal of the solvent under reduced pressure left the crude product as a solid. Chromatography on silica gel, eluting with CH2Cl2/MeOH (97/3) gave 0.2 g of the product as a solid, mp 128°-131°. The structure was confirmed by NMR and mass spectroscopy.

Calcd. for $C_{51}H_{60}N_6O_5 \cdot 0.5H_2O$ (MW 846.05): C, 72.40; H, 7.27; N, 9.93: Found C, 72.43; H, 7.31; N, 9.86.

EXAMPLE 15

DNMA-HIS-STA-(D-LEU)-NHCH2Ph

A solution of 0.67 g (0.68 mmole) of DNMA-HIS(-TOS)-STA-(D-LEU)-NHCH2Ph in 50 ml MeOH was treated with 0.58 g (3.8 mmole) of HOBT and stirred at room temperature for fifteen hours. An additional 0.58 g (3.8 mmole) of HOBT was then added and the solution stirred an additional fifteen hours. The solution was then evaporated under reduced pressure leaving a solid. This was taken up in CH2Cl2 and washed twice with saturated Na2CO3 and then with saturated NaCl. Drying and removal of the solvent under reduced pressure gave the crude product. Chromatography on silica gel, eluting with CH2Cl2/MeOH (97/3) gave 0.72 g of product, mp 186°-190°. The structure was confirmed by NMR and mass spectroscopy.

Calcd. for $C_{51}H_{60}N_6O_5 \cdot 0.5H_2O$ (MW 846.05): C, 72.40; H, 7.27; N, 9.93: Found C, 72.25; H, 7.24; N, 9.98.

EXAMPLE 16

DNMA-ASP(OCH2Ph)-CYSTA-LEU-NHCH2Ph

A solution of 3.69 g (10.8 mmole) of di-(1-naphthylmethyl)acetic acid, 6.74 g (10.8 mmole) of ASP-(OCH2Ph)-CYSTA-LEU-NHCH2Ph, and 1.47 g (10.8 mmole) of HOBT in 70 ml DMF was cooled in ice and treated with 2.26 g (10.8 mmole) of DCC in 10 ml DMF. After one-half hour at 0°, the mixture was left stirring at room temperature overnight. The urea was filtered off and the solvent removed under high vacuum. The residue was taken up in EtOAc, filtered, washed with 1N HCl, H2O, saturated NaHCO3, then saturated NaCl. Drying and removal of the solvent under reduced pressure left the crude product. Chromatography on 350 g of silica gel, eluting with CHCl3/MeOH (98/2) gave 9.38 g of product. The structure was confirmed by NMR and mass spectroscopy.

Calcd. for $C_{59}H_{68}N_4O_7 \cdot 0.6CHCl_3$ (MW 1016.80): C, 70.40; H, 6.80; N, 5.51: Found C, 70.59; H, 6.93; N, 5.58.

EXAMPLE 17

DNMA-ASP-CYSTA-LEU-NHCH2Ph

A solution of 9.1 g (9.6 mmole) of DNMA-ASP(OCH2Ph)-CYSTA-LEU-NHCH2Ph in 230 ml of MeOH was treated with 1.0 g of 20% Pd/C and stirred under a hydrogen atmosphere for six hours. The mixture was filtered and the solvent removed under reduced pressure leaving 7.29 g of the product as a foam. The structure was confirmed by mass spectroscopy.

EXAMPLE 18

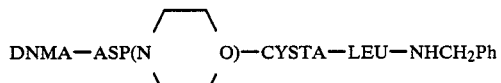

A solution of 0.5 g (0.6 mmole) of DNMA-ASP-CYSTA-LEU-NHCH2Ph in 15 ml DMF was cooled in ice and 80 mg (0.6 mmole) of HOBT added followed by 122 mg (0.6 mmole) of DCC. After stirring for ten minutes, 0.06 ml (0.6 mmole) of morpholine was added. The solution was stirred for one-half hour at 0°, then at room temperature overnight. The mixture was filtered and the DMF removed under high vacuum. The residue was taken up in EtOAc, filtered, and washed with 1N HCl, H2O, saturated NaHCO3, and saturated NaCl. Removal of the solvent under reduced pressure left the crude product as a solid. Chromatography on silica gel, eluting with EtOAc gave the product, which was recrystallized from EtOAc/hexane. There was obtained 0.2 g of product. The structure was confirmed by NMR and mass spectroscopy.

Calcd. for $C_{56}H_{69}N_5O_7 \cdot H_2O$ (MW 942.17): C, 71.38; H, 7.60; N, 7.43: Found C, 71.43; H, 7.49; N, 7.52.

EXAMPLE 19

DNMA-HIS-CYSTA-LEU-NHCH$_2$Ph

To 2.2 g (1.97 mmole) of DNMA-HIS(TRT)-CYS-TA-LEU-NHCH$_2$Ph was added 100 ml of 80% HOAc. The solution was heated on a steam bath for one hour, cooled, and the solvent removed under reduced pressure. The residue was diluted with EtOAc, washed with saturated NaHCO$_3$, dried, and concentrated to afford the crude product. Chromatography on silica gel, eluting with a gradient of 0–5% MeOH/CHCl$_3$ gave 1.55 g of the product.

Calcd. for $C_{54}H_{64}N_6O_5 \cdot 0.2CHCl_3$ (MW 900.98): C, 72.25; H, 7.18; N, 9.33: Found C, 71.98; H, 7.27; N, 9.12.

EXAMPLE 20

DNMA-(N-MeHIS)-STA-LEU-NHCH$_2$Ph

To 580 mg (0.58 mmole) of DNMA-(N-MeHIS)-(TOS)-STA-LEU-NHCH$_2$Ph in 5 ml CH$_3$OH was added 234 mg (1.73 mmole) of HOBT. The mixture was stirred at room temperature for forty-eight hours and concentrated under reduced pressure. The residue was diluted with EtOAc, washed with saturated NaHCO$_3$, dried, and concentrated under reduced pressure to afford the crude product. Chromatography on silica gel, eluting with a gradient of 0–2% MeOH in CHCl$_3$ afforded 400 mg of product.

Calcd. for $C_{52}H_{62}N_6O_5$ (MW 851.06): C, 73.38; H, 7.34; N, 9.87: Found C, 73.45; H, 7.76; N, 9.47.

EXAMPLE 21

DNMA-HIS-STA-(N-MeLEU)-NHCH$_2$Ph

To 2.8 g (2.56 mmole) of DNMA-HIS(TRT)-STA-(N-MeLEU)-NHCH$_2$Ph was added 100 ml of 80% HOAc. The mixture was heated on a steam bath for one hour and the solvent then removed under reduced pressure. The residue was diluted with EtOAc, washed with NaHCO$_3$, dried, and concentrated under reduced pressure to afford the crude product. Chromatography on silica gel, eluting with a gradient of 0–5% MeOH in CHCl$_3$ gave 2.0 g of the product.

Calcd. for $C_{52}H_{62}N_6O_5 \cdot 0.35CHCl_3$ (MW 892.85): C, 70.42; H, 7.04; N, 9.41: Found C, 70.46; H, 7.14; N, 9.28.

EXAMPLE 22

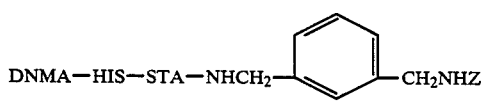

A solution of 1.85 g (1.64 mmole) of

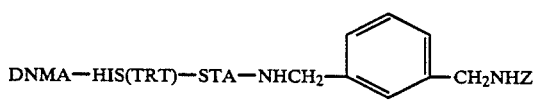

in 15 ml of 80% HOAc was heated on a steam bath for five minutes, then allowed to cool to room temperature over one hour. The solvent was removed under reduced pressure and the residue taken up in EtOAc and washed with 1N NaOH, then saturated NaCl. After drying, the solution was concentrated to a small volume and poured into excess Et$_2$O. The precipitated solid was collected and washed with Et$_2$O. There was obtained 1.25 g of the product as a white solid. The structure was confirmed by NMR and mass spectroscopy.

Calcd. for $C_{54}H_{58}N_6O_6$ (MW 887.10): C, 73.11; H, 6.59; N, 9.47: Found C, 72.89; H, 6.65; N, 9.42.

EXAMPLE 23

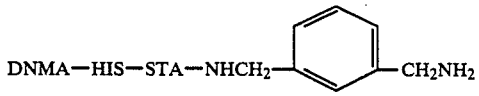

To a solution of 970 mg (1.09 mmole) of

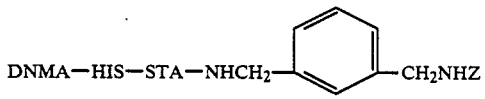

in 100 ml MeOH and 50 ml THF was added 100 mg of 20% Pd/C and the solution purged with hydrogen for three hours. An additional 100 mg of 20% Pd/C was added and the hydrogen purge continued for an additional four hours. The mixture was filtered and the solvent removed under reduced pressure leaving 880 mg of the product as a white foam. The structure was confirmed by NMR and mass spectroscopy.

Calcd. for $C_{46}H_{52}N_6O_4 \cdot 1.0CH_3OH$ (MW 785.01): C, 71.91; H, 7.19; N, 10.70: Found C, 71.82; H, 7.08; N, 10.56.

EXAMPLE 24

DNMA-HIS-STA-NHCH$_2$CH=CH$_2$

A solution of 6.86 g (20.2 mmole) of di-(1-naphthylmethyl) acetic acid and 2.87 g (21.2 mmole) of HOBT in 40 ml DMF was cooled in ice and treated with 4.37 g (21.2 mmole) of DCC followed by 7.08 g (20.2 mmole) of HIS-STA-NHCH$_2$CH=CH$_2$. The solution was kept at 4° overnight, filtered, ad the solvent removed under high vacuum. The residue was taken up in EtOAc and washed with 1N citric acid, saturated NaCl, saturated NaHCO$_3$, and saturated NaCl. Drying and removal of the solvent under reduced pressure left the crude product. Chromatography on silica gel, eluting with CHCl$_3$/MeOH (3/1) gave 4.38 g of material. NMR indicated that this contained an additional DNMA group which had acylated the imidazole portion of HIS. This material was dissolved in 100 ml MeOH and treated with 2 ml of 50% NaOH. The material was stirred at room temperature for one hour, the pH adjusted to 7, and the solvent removed under reduced pressure. The residue was taken up in EtOAc and washed with saturated NaHCO$_3$, then saturated NaCl. Drying and removal of the solvent under reduced pressure gave a residue which was taken up in warm CHCl$_3$ and poured into excess Et$_2$O. The precipitated solid was collected to give 2.19 g of product as a white solid. The structure was confirmed by NMR and mass spectroscopy.

Calcd. for $C_{41}H_{47}N_5O_4 \cdot 0.25CHCl_3$ (MW 703.67): C, 70.40; H, 6.77; N, 9.95: Found C, 70.34; H, 6.95; N, 9.46.

INTERMEDIATES FOR EXAMPLE 1

BOC-STA-LEU-NHCH$_2$Ph 1.80 g LEU-NHCH$_2$Ph.HCl [Japan 83/59952], 2.27 g BOC-STA (U.S. Pat. No. 4,397,786) and 1.04 g HOBT were dissolved in 125 ml dichloromethane and cooled to 0°. 1.07 ml of Et$_3$N was then added. A cold solution of 1.59 g DCC in 20 ml dichloromethane was added, followed by the addition of 50 ml cold DMF. The mixture was stirred at 0° for two hours, followed by 12° overnight. The mixture was then filtered, stripped to a paste, and resuspended in EtOAc. The suspension was filtered, the filtrate washed with 1N citric acid, saturated sodium chloride solution, saturated sodium bicarbonate solution, and saturated sodium chloride solution, and dried over anhydrous magnesium sulfate. The suspension was filtered and stripped to a white foam, 3.77 g, which was crystallized from ethyl ether and hexane giving a white solid, 3.41 g (92% yield), mp 89°-92°. Spectral and elemental analysis confirmed the structure. $[\alpha]_D^{23} = -34.2°$ (C, 1.06, MeOH).

STA-LEU-NHCH$_2$Ph.HCl 2.77 g BOC-STA-LEU-NHCH$_2$Ph was dissolved in 100 ml dichloromethane, which was then saturated with anhydrous hydrogen chloride gas. After stirring at 25° for one hour, the solvent was removed in vacuo, and the residue resuspended in dichloromethane, giving a crystalline solid. The suspension was diluted with ethyl ether, filtered, and the solid dried in vacuo, 2.24 g, 93% yield. Spectral and elemental analysis confirmed the structure. $[\alpha]_D^{23} = -19.1°$ (C, 1.06, MeOH).

Z-HIS(TRT)-OCH$_3$

Z-HIS-OCH$_3$ [*J. Chem. Soc.*, Perkin I, 2261 (1979)] (70 g) was dissolved in dichloromethane (500 ml) and cooled to 0°. Triethyl amine (32 ml) and then trityl chloride (64.3 g) were added and the solution allowed to stir at room temperature overnight. The mixture was washed with sodium bicarbonate and brine, dried over sodium sulfate, filtered, and evaporated. The residue was recrystallized from ethyl acetate to give 100 g of product.

Z-HIS(TRT)

Z-HIS(TRT)-OCH$_3$ (30 g) was dissolved in 300 ml of dioxane and cooled to 0°. Sodium hydroxide (2.7 g) in 80 ml of water was added. The mixture was stirred for one hour and then acidified with 1N citric acid to pH 2. The mixture was extracted with ethyl acetate. The organic phase was washed with brine, dried over sodium sulfate, filtered, and evaporated to give 27 g of product.

Z-HIS(TRT)-STA-LEU-NHCH$_2$Ph

Z-HIS(TRT) (4.65 g, 8.75 mmole) and HOBT.H$_2$O (1.24 g, 9.18 mmole) were dissolved in 5 ml DMSO, diluted to 150 ml with CH$_2$Cl$_2$, and cooled to −5°. A solution of DCC (1.9 g, 9.18 mmole) in 30 ml CH$_2$Cl$_2$ was added. A solution of STA-LEU-NHCH$_2$Ph.HCl (3.62 g, 8.75 mmole) and Et$_3$N (1.28 ml, 9.18 mmole) in 50 ml cold CH$_2$Cl$_2$ was added, and the mixture was stirred at −5°, and allowed to warm to 25° for two days. The solids were then filtered off, and the filtrate was stripped to an oil. The oil was suspended in EtOAc, washed with brine, 1N citric acid, brine, saturated NaHCO$_3$ solution, and brine. The organic phase was dried over MgSO$_4$, filtered, and stripped to an oil. The oil was dissolved in EtOAc and a precipitate was filtered off. The filtrate was diluted with Et$_2$O and stripped to give 8.17 g of the product as a foam. NMR and mass spectral analysis confirmed the structure. The product was sufficiently pure for use in the following steps.

HIS(TRT)-STA-LEU-NHCH$_2$Ph

Z-HIS(TRT)-STA-LEU-NHCH$_2$Ph (8.0 g, 8.98 mmole) was dissolved in 200 ml MeOH to which was added 0.50 g 20% Pd on charcoal catalyst. The suspension was purged with H$_2$ gas over 3.5 hours, filtered, and stripped to a glass, 7:31 g. The crude material was chromatographed on silica gel, eluting with a gradient of 2 to 5% MeOH in CHCl$_3$, giving a white foam, 5.74 g. NMR and mass spectral analysis confirmed the structure of the product.

DNMA-HIS(TRT)-STA-LEU-NHCH$_2$Ph

Di-(1-naphthylmethyl)acetic acid (0.65 g, 1.91 mmole) and HOBT.H$_2$O (0.271 g, 2.0 mmole) were dissolved in 4 ml DMF, diluted to 30 ml with CH$_2$Cl$_2$ and cooled to 0°. DCC (0.414 g, 2.0 mmole) was added, followed by a solution of HIS(TRT)-STA-LEU-NHCH$_2$Ph (1.52 g, 1.91 mmole) in 20 ml CH$_2$Cl$_2$. The mixture was stirred and allowed to warm to 25° overnight. The mixture was filtered, and the solvent removed in vacuo. The residue was dissolved in EtOAc and washed with 1N citric acid, brine, saturated NaHCO$_3$ solution, and brine. The organic phase was dried over MgSO$_4$, filtered, and stripped to a foam, 2.05 g. The foam was chromatographed on silica gel, eluting with a gradient of 0 to 2% MeOH in CHCl$_3$. Combining the appropriate fractions using Et$_2$O gave 1.47 g of the product as a white foam. NMR, IR, and mass spectral analysis confirmed the structure of the product.

INTERMEDIATES FOR EXAMPLE 2

BOC-STA-NHCH$_2$CH(CH$_3$)CH$_2$CH$_3$

BOC-STA (27.53 g, 0.1 mole, U.S. Pat. No. 4,397,786) and HOBT.H$_2$O (14.2 g, 0.105 mole) were dissolved in 40 ml DMF. 300 ml CH$_2$Cl$_2$ was added, and the mixture was cooled to 0°. A solution of DCC (21.66 g, 0.105 mole) in 50 ml CH$_2$Cl$_2$ was added, followed by S-2-methylbutylamine (12 ml, 0.1 mole). After stirring at 0° for two hours, the mixture was allowed to warm to 25° over 1.5 hours. The mixture was filtered and the solvent was removed in vacuo. The residue was dissolved in EtOAc, which was washed with 1N citric acid, brine, saturated NaHCO$_3$ solution, and brine. The organic phase was dried over MgSO$_4$, filtered, and stripped to a gum, 36.90 g. The gum was dissolved in Et$_2$O and treated with charcoal to remove colored impurities. The suspension was filtered and stripped to a gum, 35.2 g, which was suitable for use in the following procedure without further purification.

STA-NHCH$_2$CH(CH$_3$)CH$_2$CH$_3$.HCl

BOC-STA-NHCH$_2$CH(CH$_3$)CH$_2$CH$_3$ (34.4 g, 0.1 mole) was dissolved in 250 CH$_2$Cl$_2$ and the solution was purged occasionally with anhydrous HCl gas over three hours. A solid precipitated from solution which was filtered, washed with CH$_2$Cl$_2$, and dried at 40° in vacuo to a hygroscopic solid, 21 g. The solid was triturated with a mixture of CH$_2$Cl$_2$/Et$_2$O, filtered, and dried at 40° in vacuo to a white solid, 19.34 g. Spectral analysis confirmed the structure.

Z-HIS(TRT)-STA-NHCH₂CH(CH₃)CH₂CH₃

Z-HIS(TRT) (4.37 g, 8.22 mmole) and HOBT.H₂O (1.17 g, 8.63 mmole) were dissolved in 10 ml DMF, diluted to 50 ml with CH₂Cl₂, and cooled to −2°. A solution of DCC (1.78 g, 8.63 mmole) in 20 ml CH₂Cl₂ was added, followed by a solution of STA-NHCH₂CH(CH₃)CH₂CH₃.HCl (1.72 g, 6.12 mmole) in a mixture of 10 ml DMF, 10 ml CH₂Cl₂ and Et₃N (1.20 ml, 8.63 mmole). The mixture was stirred at 0° and allowed to warm to 25° overnight. The mixture was filtered, stripped to an oil, and the residue dissolved in a mixture of EtOAc and Et₂O. The solution was washed with 1N citric acid, brine, saturated NaHCO₃ solution, and brine, followed by drying over MgSO₄, filtration, and stripping to a foam, 5.62 g. The foam was chromatographed on silica gel, eluting with a gradient of 0 to 3% MeOH in CHCl₃. The product was recovered as a foam, 3.15 g. IR, NMR, and mass spectral analysis confirmed the structure.

HIS(TRT)-STA-NHCH₂CH(CH₃)CH₂CH₃

A solution of Z-HIS(TRT)-STA-NHCH₂CH(CH₃)CH₂CH₃ (2.91 g, 3.84 mmole) in 80 ml MeOH was treated with 20% Pd on charcoal (0.13 g) and was then purged with hydrogen gas for seven hours. The mixture was filtered, stripped to an oil, redissolved in Et₂O/hexane and stripped to a foam, 2.39 g. The material was sufficiently pure to use in the following step. IR, NMR, and mass spectral analysis confirmed the structure.

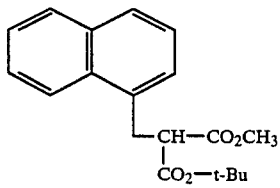

washed with 1N citric acid, brine, saturated NaHCO₃, brine, and then dried over MgSO₄. The solution was filtered and stripped to a yellow oil, 58.84 g. The product was used in the following step without further purification.

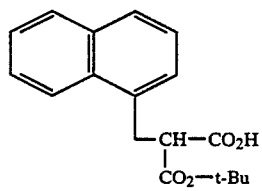

A solution of 61 g (0.194 mole) of crude

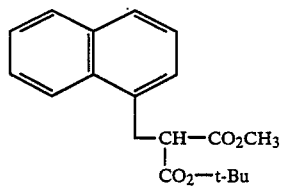

in 250 ml of MeOH was treated with 40 g of 50% NaOH solution and stirred for five hours forming a paste. The mixture was filtered, washed with MeOH, and the filtrate stripped to a paste. The paste was taken up in H₂O and washed with Et₂O. The pH was adjusted to 2.0 with dilute HCl and the mixture extracted with Et₂O. The Et₂O was washed with brine, dried over MgSO₄, filtered, and stripped to an oil, 22.19 g. This was dissolved in CHCl₃ and a crystalline solid filtered off. Removal of the solvent under reduced pressure gave 13.8 g of a syrup. Chromatography on silica gel, eluting with EtOAc/hexane (1:1) gave the product as a foam. IR, NMR, and mass spectral analysis confirmed the structure.

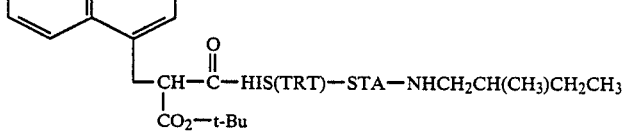

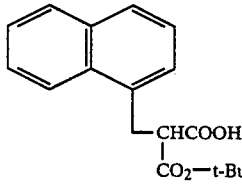

NaH (10.46 g, 50% emulsion in oil, 0.218 mole) was washed with dry THF to remove the oil. The residue was suspended in 500 ml THF to which was added a solution of t-butyl methyl malonate (34.5 g, 0.198 mole) in 50 ml THF. A vigorous reaction ensued, giving a paste-like precipitate. After heating at reflux for thirty minutes, the mixture was cooled to 35° and 1-chloromethylnaphthalene (35.0 g, 0.198 mole) was added. The mixture was stirred at 40° overnight, stripped to a paste, and the residue taken up in EtOAc. The suspension was HIS(TRT)-STA-NHCH₂CH(CH₃)CH₂CH₃ (3.12 g, 5.0 mmole) and HOBT.H₂O (0.21 g, 5.25 mmole) were dissolved in 80 ml DMF and cooled to 0°. DCC (1.08 g, 5.25 mmole) was added, and the mixture was stirred overnight at 25°. The mixture was filtered and stripped to a syrup in vacuo, which was taken up into EtOAc. The solution was washed with 1N citric acid, brine, saturated NaHCO₃ solution, and brine. The solution was dried over MgSO₄, filtered, and stripped to a foam, 4.85 g. The foam was chromatographed on silica gel, eluting with 2% MeOH in EtOAc. The product was recovered as a foam, 3.50 g. Mass spectral analysis confirmed the structure.

INTERMEDIATES FOR EXAMPLE 3

BOC-NHCH$_2$CH=CH$_2$

Di-t-butyldicarbonate (43.65 g, 0.2 mole) was dissolved in 250 ml CH$_2$Cl$_2$, to which was added allyl amine (15.0 ml, 0.2 mole) in a dropwise manner. After stirring overnight, the mixture was stripped to an oil, dissolved in EtOAc, and washed with 1N citric acid, brine, saturated NaHCO$_3$ solution, and brine. The solution was dried over MgSO$_4$, filtered, and stripped to an oil which crystallized, 30.02 g. NMR confirmed the structure.

A solution of 21.72 g (0.138 mole) of BOC-allylamine in 250 ml of CH$_2$Cl$_2$ was treated with 28 g (0.138 mole) of m-chloroperbenzoic acid causing a mild exotherm. After stirring overnight the mixture was filtered and the filtrate washed with 10% sodium sulfite solution, 1N citric acid, saturated NaHCO$_3$, and brine. Drying over MgSO$_4$, filtering, and removing the solvent under reduced pressure left 25.0 g of the crude product as an oil. Chromatography on silica gel, eluting with 75/25 hexane/EtOAc gave 17.1 g of a clear oil. NMR, IR, and mass spectral analysis confirmed the structure.

BOC-NHCH$_2$CH(OH)CH$_2$SCH(CH$_3$)$_2$

NaH (3.18 g, 50% emulsion in oil, 0.066 mole) was washed free of oil with dry THF and was suspended in 100 ml DMF. Isopropyl mercaptan (14.0 ml, 0.151 mole) was added slowly. Solution occurred after stirring thirty minutes. The mixture was cooled to 25° and

(11.5 g, 0.066 mole) was added as a solution in 30 ml THF. The mixture was stirred overnight and the pH was then adjusted to 7 with 12% HCl. The solvent was removed in vacuo. The residue was taken up in EtOAc, washed with brine, 1N citric acid, brine, saturated NaHCO$_3$ solution, and brine. The EtOAc solution was dried over MgSO$_4$, filtered, and stripped to an oil, 15.84 g. The product was chromatographed on silica gel, eluting with 50/50 hexane/EtOAc, giving an oil, 14.85 g. IR, NMR, and mass spectral analysis confirmed the structure.

H$_2$N-CH$_2$CH(OH)CH$_2$SCH(CH$_3$)$_2$.HCl

BOC-NHCH$_2$CH(OH)CH$_2$SCH(CH$_3$)$_2$ (3.74 g, 0.015 mole) was dissolved in 75 ml CH$_2$Cl$_2$ and occasionally purged with HCl gas over two hours. The solvent was removed in vacuo, and the residue was triturated with Et$_2$O. The solvent was decanted and the residue was stripped to a foam, 2.83 g. IR, NMR, and mass spectral analysis confirmed the structure.

BOC-STA-OCH$_3$

BOC-STA (35.9 g, 0.13 mole, U.S. Pat. No. 4,397,786) was dissolved in 1 l EtOAc. An ethereal solution of diazomethane (prepared from 52 g p-tolylsulfonylmethylnitrosamide per *Organic Synthesis*, Collective Volume 4, pp. 251-3) was added to the EtOAc solution until a slight yellow color persisted. After stirring at 25° for two hours, HOAc was added until the yellow color disappeared. After stirring thirty minutes, the solvent was removed in vacuo giving the product as a crystalline solid, 40.1 g.

STA-OCH$_3$.HCl

BOC-STA-OCH$_3$ (37.4 g, 0.13 mole) was dissolved in 600 ml CH$_2$Cl$_2$ which was occasionally purged with anhydrous HCl gas over four hours. When thin layer chromatography indicated complete consumption of the starting material, the solvent was removed in vacuo and the residue resuspended in CH$_2$Cl$_2$/Et$_2$O, which gave a crystalline solid, 30.8 g. The material was sufficiently pure for use in the following steps.

Z-HIS(TRT)-STA-OCH$_3$

Z-HIS(TRT) (28.97 g, 0.0545 mole) and HOBT.H$_2$O (7.73 g, 0.0572 mole) were dissolved in 250 ml DMF and cooled to 0°. STA-OCH$_3$.HCl (12.3 g, 0.0545 mole) was added as a solution in 75 ml DMF containing Et$_3$N (7.97 ml, 0.0572 mole). To the mixture was added a cold solution of DCC (11.81 g, 0.0572 mole) in 50 ml DMF. After warming from 0° to 25° over five hours, the mixture was refrigerated overnight at 4°. The mixture was filtered, stripped to an oil, and taken up into EtOAc. The solution was washed with 1N citric acid, brine, saturated NaHCO$_3$ solution, and brine. The solution was dried over MgSO$_4$, filtered, and stripped to an oil. The oil was chromatographed on silica gel, eluting with a gradient of 0 to 5% MeOH in CHCl$_3$, giving the product as a white solid, 30.7 g.

HIS(TRT)-STA-OCH$_3$

Z-HIS(TRT)-STA-OCH$_3$ (10.0 g, 0.0142 mole) and 20% Pd on charcoal catalyst (0.5 g) were added to 200 ml MeOH, which was then purged with hydrogen gas over five hours. The mixture was filtered and stripped to a foam, 8.03 g. IR, NMR, and mass spectral analysis confirmed the structure.

DNMA-HIS(TRT)-STA-OCH$_3$

Di-(1-naphthylmethyl)acetic acid (2.63 g, 7.73 mmole), HOBT.H$_2$O (0.834 g, 8.25 mmole), HIS(TRT)-STA-OCH$_3$ (4.32 g, 7.73 mmole), and DCC (1.70 g, 8.25 mmole) were dissolved in 100 ml DMF and stirred at 25° for sixteen hours. The mixture was filtered, stripped to an oil, and the residue was taken up into EtOAc. The solution was washed with 1N citric acid, saturated NaHCO$_3$ solution, and brine, followed by drying over MgSO$_4$, filtering, and stripping to a yellow foam, 7.19 g. The foam was chromatographed on silica gel, eluting with EtOAc, and giving a foam, 4.60 g. NMR and mass spectral analysis confirmed structure.

DNMA-HIS(TRT)-STA

DNMA-HIS(TRT)-STA-OCH$_3$ (3.1 g, 3.44 mmole) and NaOH (0.20 g, 5.16 mmole) were dissolved in a mixture of 50 ml dioxane and 56 ml H$_2$O. After five hours, the pH was adjusted to 7 with 1N HCl. The solvent was removed in vacuo and the residue was taken up into EtOAc. The solution was washed with 1N citric acid and brine, dried over MgSO4, filtered, and stripped to reduced volume. Addition of Et2O gave a precipitate which was filtered off and dried to give a solid, 2.15 g. The structure of the product was confirmed by mass spectral analysis.

DNMA-HIS(TRT)-STA-NHCH2CH(OH)CH2SCH(CH3)2

DNMA-HIS(TRT)-STA (0.65 g, 0.74 mmole) and HOBT.H2O (0.105 g, 0.78 mmole) were dissolved in 10 ml DMF. H2N-CH2CH(OH)CH2SCH(CH3)2.HCl (0.138 g, 0.74 mmole) was added as a solution in a mixture of 5 ml DMF and Et3N (0.109 ml, 0.78 mmole). DCC (0.16 g, 0.78 mmole) was added, and the mixture was stirred overnight. The mixture was filtered, stripped, and the residue was taken up into EtOAc. The solution was washed with 1N citric acid, brine, saturated NaHCO3 solution, and brine. The solution was dried over MgSO4, filtered, and stripped to a foam, 0.81 g. The foam was chromatographed on silica gel, eluting with 2% MeOH in CHCl3, and giving the product as a white foam, 0.50 g. Mass spectral analysis confirmed the structure.

INTERMEDIATES FOR EXAMPLE 4

BOC-NHCH2CH(OH)CH2SO2CH(CH3)2

BOC-NHCH2CH(OH)CH2SCH(CH3)2 (3.74 g, 0.015 mole) and m-chloroperbenzoic acid (7.76 g, 0.045 mole) were dissolved with cooling in 100 ml CH2Cl2. The mixture was stirred at 25° overnight, and stripped to a solid. The solid was dissolved in EtOAc, washed with 10% sodium sulfite solution, saturated NaHCO3 solution, and brine. The solution was dried over MgSO4, filtered, and stripped to an oil, 4.15 g. The oil was chromatographed on silica gel, eluting with 50/50 hexane/EtOAc, and giving the product as an oil, 3.66 g. NMR and mass spectral analysis confirmed the structure.

H2N-CH2CH(OH)CH2SO2CH(CH3)2.HCl

BOC-NHCH2CH(OH)CH2SO2CH(CH3)2 (3.19 g, 11.35 mmole) was dissolved in 75 ml CH2Cl2 and purged with HCl gas over two hours. The mixture was stripped, triturated with ethyl ether, and filtered. The solid was washed with ethyl ether and dried giving 2.21 g of product.

DNMA-HIS(TRT)-STA-NHCH2CH(OH)CH2SO2CH(CH3)2

DNMA-HIS(TRT)-STA (0.59 g, 0.67 mmole) and HOBT.H2O (0.095 g, 0.71 mmole) were dissolved in 10 ml DMF. A solution of H2N-CH2CH(OH)CH2SO2CH(CH3)2.HCl (0.146 g, 0.67 mmole) in 10 ml DMF and Et3N (0.11 ml, 0.71 mmole) was added, followed by DCC (0.15 g, 0.71 mmole). The mixture was stirred at 25° overnight, stripped, and the residue taken up into EtOAc. The suspension was washed with 1 N citric acid, brine, saturated NaHCO3 solution, and brine. The solution was dried over MgSO4, filtered, and stripped to a foam, 0.81 g. The foam was chromatographed on silica gel, eluting with 2% MeOH in CHCl3, and giving the product as a white foam, 0.63 g. Mass spectral analysis confirmed the structure.

INTERMEDIATES FOR EXAMPLES 5 AND 6

Aminomalonic Acid, Methyl Benzyl Ester

Methyl, benzyl isonitrosomalonate was prepared from 97 g of methyl, benzyl malonate by the procedure described in Org. Syn. Coll. Vol. 5, p. 373. The 100 g of crude product obtained was reduced to the amino derivative by the procedure described in J. Am. Chem. Soc., 75, 1970 (1953). The 94 g of crude product was used in the following step without further purification.

BOC-Aminomalonic Acid, Methyl Benzyl Ester

A solution of 94 g of aminomalonic acid, methyl benzyl ester in 750 ml Et2O was cooled to 5° and treated with 91.66 g of di-t-butyldicarbonate. After standing at 4° overnight, the solvent was removed under reduced pressure giving an oil. Chromatography on silica gel, eluting with hexane/EtOAc (85/15) gave 66.97 g (49% yield) of the product as an oil which solidified on standing. The structure was confirmed by NMR and mass spectroscopy.

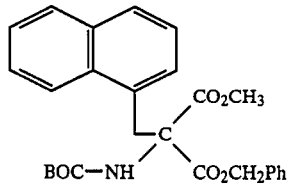

To a solution of 6.87 g (21.25 mmole) of BOC-aminomalonic acid, methyl, benzyl ester in 75 ml of THF was added 1.02 g (21.25 mmole) of 50% NaH emulsion in oil. The mixture was stirred for one hour, giving solution. A solution of 4.93 g (22.3 mmole) 1-bromomethylnaphthalene in 30 ml THF was added, and the mixture was stirred overnight at ambient temperature. The solvent was removed under reduced pressure, the residue taken up in EtOAc and washed with 1N citric acid, saturated NaCl, saturated NaHCO3 and saturated NaCl. Drying and removal of the solvent under reduced pressure left 9.21 g of the crude product. Chromatography on silica gel, eluting with hexane/EtOAc (85/15), gave 4.55 g of th product as a foam. The structure was confirmed by mass spectroscopy.

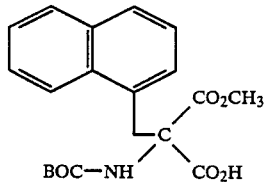

To a solution of 4.35 g (9.38 mmole) BOC-amino-α-(1-nphthylmethyl)malonic acid, methyl, benzyl ester in 200 ml MeOH was added 0.36 g of 20% Pd/C, followed by purging with hydrogen for two hours. The mixture was filtered and evaporated under reduced pressure to give 3.33 g of the product as a foam, suitable for use in the following reaction. The structure was confirmed by mass spectroscopy.

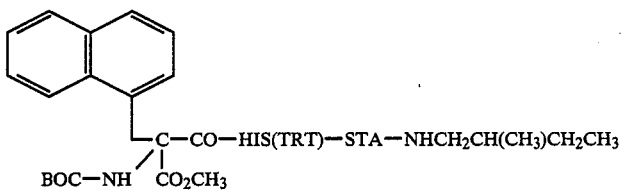

A solution of 0.75 g (2.0 mmole) of BOC-amino-α-(1-naphthylmethyl)malonic acid, methyl ester in 40 ml DMF was treated with 1.25 g (2.0 mmole) HIS(TRT)-STA-NHCH2CH(CH3)CH2CH3, 0.283 g (2.1 mmole) HOBT, and 0.43 g (2.1 mmole) DCC. After stirring at 12° for one hour, the mixture was allowed to warm to room temperature overnight. The mixture was evaporated under reduced pressure to an oil which was taken up in EtOAc. The solution was washed with 1N citric acid, saturated NaCl, saturated NaHCO3, and saturated NaCl. The organic phase was dried and evaporated under reduced pressure, leaving 1.96 g of crude product as a foam. Chromatography on silica gel, eluting with a gradient of 0–5% MeOH in CHCl3, gave 1.48 g of the product as a foam. The structure was confirmed by mass spectroscopy.

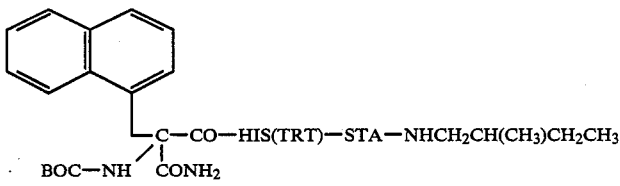

A solution of 0.36 g (0.368 mmole) of

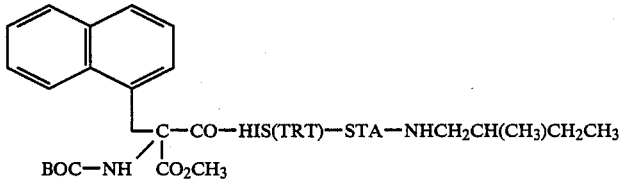

in 50 ml MeOH was cooled to −5° and saturated with NH3 gas, then allowed to warm to room temperature overnight. This procedure was repeated several times until thin layer chromatography showed complete consumption of the starting material. The solvent was removed under reduced pressure and the residue chromatographed on silica gel, eluting with CHCl3/MeOH (99/1). There was obtained 0.22 g of the product as a white solid. The structure was confirmed by mass spectroscopy.

INTERMEDIATE FOR EXAMPLES 7, 8, 22, AND 23

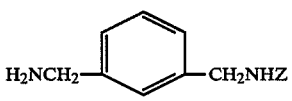

A solution of 20.4 g (150 mmole) of m-xylylenediamine in 500 ml dichloromethane was cooled to −78° and a solution of 40.4 g (162 mmole) of N-(benzyloxycarbonyloxy)succinimide in 200 ml CH2Cl2 was added over two hours. The mixture was stirred and allowed to warm to room temperature over three days. The mixture was evaporated under reduced pressure to a paste, taken up in EtOAc, and washed with 1N HCl. The aqueous phase was adjusted to pH 12 by addition of 50% NaOH and was extracted with EtOAc. The organic phase was washed with saturated NaCl, dried, and the solvent was removed under reduced pressure to give 28.7 g of the product as an oil. The structure was confirmed by NMR and mass spectroscopy.

INTERMEDIATES FOR EXAMPLES 7 AND 8

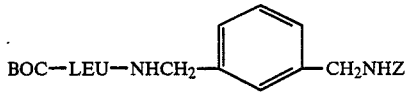

A solution of 7.48 g (30 mmole) BOC-LEU.H2O in 100 ml THF/CH2Cl2 (50/50) was dried over anhydrous MgSO4, filtered, and evaporated to an oil. The oil was dissolved in 100 ml DMF, to which was added 8.11 g (30 mmole) of

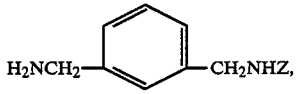

and 4.26 g (31 mmole) HOBT. The solution was cooled to -5° and 6.5 g (31 mmole) DCC was added with stirring, allowing the mixture to warm to room temperature overnight. The mixture was filtered, the solvent removed under high vacuum, and the residue taken up in EtOAc. The solution was washed with 1N citric acid, saturated NaCl, saturated Na2CO3, and saturated NaCl. After drying, the solvent was removed under reduced pressure giving a solid. The solid was triturated with Et₂O, filtered, and washed with Et₂O. There was obtained 9.85 g of the product, of sufficient purity for use in the following reaction. The structure was confirmed by NMR and mass spectroscopy.

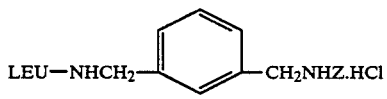

A solution of 5.0 g (10.3 mmole) of

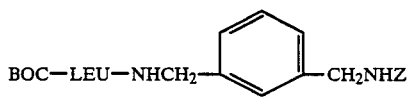

in 150 ml CH₂Cl₂ was purged with HCl gas occasionally over two hours. The solvent was removed under reduced pressure, and the residue was triturated with Et₂O. The suspension was filtered, and the solids were again triturated, filtered, and dried to a brittle foam, 4.76 g. The product was of sufficient purity for use in the following reaction. The structure was confirmed by NMR and mass spectroscopy.

INTERMEDIATES FOR EXAMPLES 9 AND 10

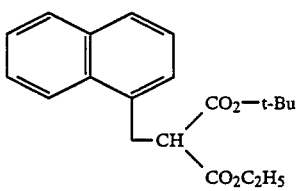

A suspension of 2.45 g (61.2 mmole) of sodium hydride (60% dispersion in mineral oil) in 5 ml THF was stirred and the THF decanted. An additional 150 ml of THF was then added to the suspension. A solution of 11.46 g (61.2 mmole) of t-butyl ethyl malonate in 50 ml of THF was added and the mixture stirred. Solution occurred after 45 minutes. This was then treated with 13.54 g (61.2 mmole) of 1-bromomethylnaphthalene in 100 ml THF and the mixture stirred at room temperature overnight. The THF was removed under reduced pressure, the residue taken up in EtOAc, and washed with saturated NaCl, 1N citric acid, saturated NaHCO₃, then saturated NaCl. Drying and removal of the solvent under reduced pressure gave an oil. After chromatography on silica gel, eluting with hexane/EtOAc (95/5), there was obtained 12.9 g of the product as an oil. The structure was confirmed by NMR and mass spectroscopy.

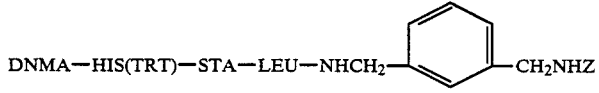

A solution of 1.70 g (1.94 mmole) DNMA-HIS(TRT)-STA and 0.27 g (2.03 mmole) HOBT in 25 ml DMF was cooled to −5°. A solution of 0.81 g (1.94 mmole) of

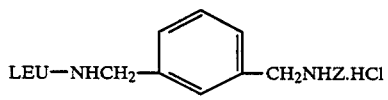

in 20 ml DMF and 0.3 ml (2.03 mmole) Et₃N was cooled and added to the previously prepared solution. 0.42 g (2.03 mmole) DCC was added, and the mixture was stirred at 0°, warmed to 25° over three hours, then stored at 4° overnight. The mixture was filtered, and the solvent removed under high vacuum. The residue was taken up in EtOAc, and washed with 1N citric acid, saturated NaCl, saturated NaHCO₃, and saturated NaCl. After drying, the mixture was evaporated to a foam under reduced pressure. The foam was chromatographed on silica gel, eluting with a gradient of 0 to 5% MeOH in CHCl₃. There was obtained 1.81 g of the product as a white foam. The structure was confirmed by mass spectroscopy.

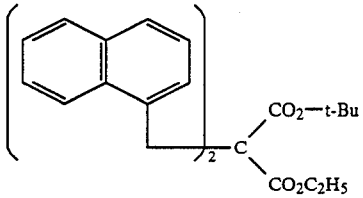

A suspension of 1.51 g (37.9 mmole) of sodium hydride (60% dispersion in mineral oil) in 15 ml DMSO was warmed to 75° for one hour giving solution. The solution was diluted with 200 ml THF and 12.4 g (37.9 mmole) of α-(1-naphthylmethyl)malonic acid, t-butyl, ethyl ester added and the solution stirred for fifteen minutes. This was then treated with a solution of 8.38 g (37.9 mmole) of 1-bromomethylnaphthalene in 100 ml THF and stirred at room temperature overnight. Glacial HOAc was added to pH 5, the mixture filtered, and the THF removed under reduced pressure. The residue was taken up in Et₂O and washed with 1N citric acid, saturated NaHCO₃, then saturated NaCl. After drying and removal of the solvent under reduced pressure, the residue was recrystallized from Et₂O/hexane There was obtained 12.54 g of the product as a white solid. The structure was confirmed by NMR and mass spectroscopy.

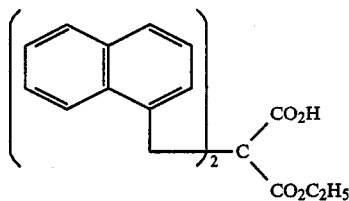

A solution of 12.3 g of di-α-(1-naphthylmethyl)malonic acid, t-butyl, ethyl ester in 100 ml Et$_2$O and 50 ml THF was saturated with HCl gas and stirred at room temperature overnight. The solvent was removed under reduced pressure and the residue crystallized from CHCl$_3$/hexane to give 9.66 g of the product as a white solid. The structure was confirmed by NMR and mass spectroscopy.

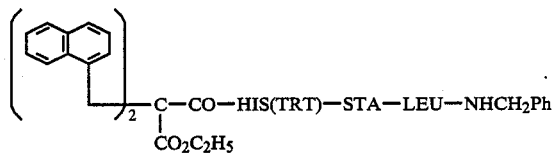

A solution of 1.24 g (3.0 mmole) of di-α-(1-naphthylmethyl)malonic acid, mono ethyl ester and 425 mg (3.0 mmole) of HOBT in 4 ml DMF and 30 ml CH$_2$Cl$_2$ was cooled to −5° and treated with a solution of 650 mg (3.0 mmole) of DCC in 5 ml of CH$_2$Cl$_2$ followed by a solution of 2.4 g (3.0 mmole) of HIS(TRT)-STA-LEU-NHCH$_2$Ph in 20 ml CH$_2$Cl$_2$. The solution was allowed to warm to room temperature overnight. The mixture was filtered and the solvent removed under reduced pressure. The residue was taken up in EtOAc and washed with 1N citric acid, saturated NaCl, saturated NaHCO$_3$, then saturated NaCl. Drying and removal of the solvent under reduced pressure gave the crude product. After chromatography on silica gel, eluting with CHCl$_3$/MeOH (95/5) there was obtained 2.91 g of pure product as a white foam. The structure was confirmed by NMR and mass spectroscopy.

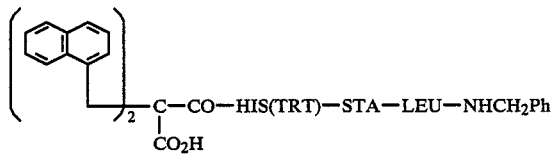

A solution of 1.44 g (1.25 mmole) of

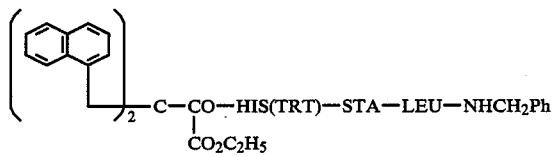

in 30 ml MeOH was treated with 3.1 g NaOH and allowed to stir at room temperature overnight. The solution was filtered and the crude product precipitated by addition of 1N HCl. The crude product was collected and recrystallized from acetone/H$_2$O to give 1.17 g of product as a white solid. The structure was confirmed by mass spectroscopy.

INTERMEDIATES FOR EXAMPLES 11 AND 12

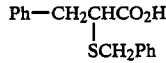

A solution of 12.5 ml of benzylmercaptan in 750 ml of liquid ammonia was treated dropwise with 22.8 g of 2-bromo-3-phenylpropionic acid and the solution stirred while the ammonia was allowed to evaporate. The residue was taken up in 10% sodium carbonate and washed with CH$_2$Cl$_2$. The aqueous phase was acidified with dilute HCl and extracted with CH$_2$Cl$_2$. Drying and removal of the solvent under reduced pressure gave the crude product. Chromatography on silica gel, eluting with a gradient of 0–2% MeOH in CH$_2$Cl$_2$ gave 22.4 g of product as a white solid, mp 53°–55°. The structure was confirmed by NMR spectroscopy.

BOC-HIS(TRT)-STA-LEU-NHCH$_2$Ph

A solution of 2.5 g (4.8 mmole) of BOC-HIS(TRT), 0.65 g (4.8 mmole) of HOBT, and 2.0 g (4.8 mmole) of STA-LEU-NHCH$_2$Ph.HCl in 200 ml of CH$_2$Cl$_2$/DMF (50/50) was cooled in ice and 0.8 ml (5.7 mmole) of Et$_3$N added, followed by 1.0 g (4.8 mmole) of DCC. After stirring at 0° for one hour, the mixture was allowed to stir at room temperature overnight. The mixture was filtered and the solvent removed under high vacuum. The residue was taken up in EtOAc, washed with 1N citric acid then Na$_2$CO$_3$ solution, then dried. Removal of the solvent under reduced pressure and chromatography of the residue on silica gel, eluting with CH$_2$Cl$_2$/MeOH (90/10) gave 4.1 g of the product as a white foam. The structure was confirmed by NMR and mass spectroscopy.

HIS-STA-LEU-NHCH$_2$Ph

A solution of 2.0 g (2.3 mmole) of BOC-HIS(TRT)-STA-LEU-NHCH$_2$Ph in 30 ml of TFA was allowed to stand for two hours, and the TFA was then removed under reduced pressure. The residue was taken up in EtOAc and washed with 1N NaOH. Drying and removal of the solvent under reduced pressure gave the crude product. Chromatography on silica gel, eluting with a gradient of 0–50% MeOH in CH$_2$Cl$_2$ gave 0.47 g of the product as a white foam. The structure was confirmed by NMR and mass spectroscopy.

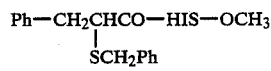

A solution of 6.13 g (22.5 mmole) of 2-benzylmercapto-3-phenylpropionic acid, 3.03 g (22.4 mmole) of HOBT, and 5.44 g (22.5 mmole) of HIS-OCH$_3$.2HCl in 300 ml of CH$_2$Cl$_2$ was cooled to 0° and 8.0 ml (57.4 mmole) of Et$_3$N added followed by 4.66 g (22.6 mmole) of DCC. After stirring for one hour at 0° the mixture was left stirring at room temperature for two days. The mixture was filtered and the filtrate evaporated under reduced pressure. The residue was taken up in EtOAc and washed with H$_2$O, Na$_2$CO$_3$ solution, then saturated NaCl. After drying and removal of the solvent under reduced pressure, the residue was chromatographed on silica gel, eluting with a gradient of 0–5% MeOH in CH₂Cl₂. There was obtained 9.28 g of the product as an oil which crystallized. The structure was confirmed by NMR and mass spectroscopy.

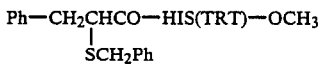

A solution of 1.45 g (3.4 mmole) of

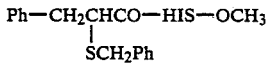

in 50 ml of CH₂Cl₂ was treated with 0.7 ml (5.0 mmole) of Et₃N followed by 1.07 g (3.8 mmole) of triphenylmethyl chloride. The solution was stirred at room temperature for two days, then washed with saturated NaHCO₃, and dried. Removal of the solvent under reduced pressure gave an oil which was chromatographed on silica gel, eluting with CH₂Cl₂/MeOH (99/1). There was obtained 2.06 g of the product as a foam. The structure was confirmed by NMR spectroscopy.

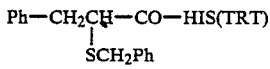

A solution of 1.86 g (2.8 mmole) of

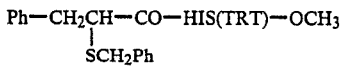

in 20 ml of MeOH was treated with 3.3 ml (3.3 mmole) of 1N NaOH and stirred at room temperature for two hours. The solvent was then removed under reduced pressure and the residue taken up in H₂O and washed with EtOAc. The aqueous phase was acidified with 1N citric acid and extracted into EtOAc. The EtOAc was washed with saturated NaCl and dried. Removal of the solvent under reduced pressure gave the crude product which was chromatographed on silica gel, eluting with CH₂Cl₂/MeOH (9/1). There was obtained 0.89 g of the product as a white foam. The structure was confirmed by NMR and mass spectroscopy.

BOC-CYSTA-NHCH₂CH(CH₃)CH₂CH₃

A solution of 6.78 g (21.5 mmole) of BOC-CYSTA and 2.9 g (21.5 mmole) of HOBT in 100 ml DMF was cooled in ice and 4.48 g (21.5 mmole) of DCC in 10 ml DMF added, followed by 1.88 g (21.5 mmole) of S-(−)-1-amino-2-methylbutane. Keep at 0° for one-half hour, then let stir at room temperature overnight. The mixture was filtered and the solvent removed under high vacuum. The residue was taken up in EtOAc and washed with 1N HCl, saturated NaHCO₃, and saturated NaCl. Drying and removal of the solvent under reduced pressure gave the crude product. Chromatography on silica gel, eluting with CHCl₃/MeOH (99/1) gave 8.2 g of the product as an oil. The structure was confirmed by mass spectroscopy.

CYSTA-NHCH₂CH(CH₃)CH₂CH₃·HCl

A solution of 8.2 g (21.3 mmole) of BOC-CYSTA-NHCH₂CH(CH₃)CH₂CH₃ in 85 ml of CH₂Cl₂ was saturated with HCl gas, stirred for one hour, then resaturated with HCl gas and allowed to stir for an additional three hours. The solution was diluted with Et₂O and the precipitated solid collected and dried. There was obtained 5.47 g of the product as a white solid. The structure was confirmed by mass spectroscopy.

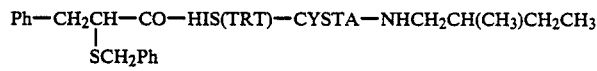

A solution of 350 mg (0.53 mmole) of

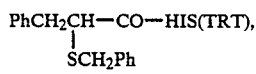

172 mg (0.53 mmole) of CYSTA-NHCH₂CH(CH₃)CH₂CH₃·HCl, and 72.6 mg (0.53 mmole) of HOBT in 15 ml DMF was cooled in ice and 0.8 ml (0.6 mmole) of Et₃N added followed by 110 mg (0.53 mmole) of DCC in 5 ml of DMF. The solution was kept at 0° for one hour, then at room temperature overnight. The solvent was removed under high vacuum and the residue brought up in EtOAc, the EtOAc solution filtered, and then washed with 1N HCl, saturated NaHCO₃, then saturated NaCl. Drying and removal of the solvent under reduced pressure gave the crude product. Chromatography on silica gel, eluting with CHCl₃/MeOH (99/1) gave 0.47 g of product of sufficient purity to use in the next reaction. The structure was confirmed by NMR and mass spectroscopy.

INTERMEDIATES FOR EXAMPLE 13

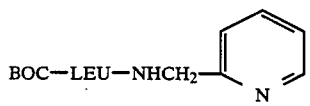

A solution of 15.52 g (62.2 mmole) BOC-LEU·H₂O in 200 ml THF/CH₂Cl₂ (50/50) was dried over anhydrous MgSO₄, filtered, and evaporated to an oil. The oil was dissolved in 200 ml DMF, to which was added 8.82 g (65.4 mmole) HOBT. After cooling to −5°, a solution of 13.48 g (65 mmole) DCC in 30 ml DMF was added, followed by 6.8 ml (62.2 mmole) of 2-aminomethylpyridine. The mixture was stirred and allowed to warm to room temperature overnight. The mixture was filtered, and the solvent was removed under high vacuum. The residue was taken into EtOAc and washed with 1N citric acid, saturated NaCl, saturated NaHCO₃, and saturated NaCl. After drying, the solvent was removed under reduced pressure, and the residue was chromatographed on silica gel, eluting with a gradient of 0 to 5% MeOH in CHCl₃. There was obtained 16.8 g of a solid of sufficient purity for use in the following reaction. The structure was confirmed by NMR and mass spectroscopy.

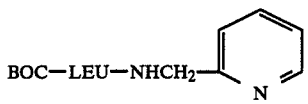

A solution of 6.41 g (19.9 mmole) of

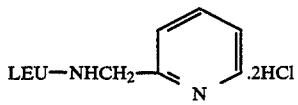

in 80 ml CH$_2$Cl$_2$ was occasionally purged with HCl gas over three hours, then evaporated under reduced pressure leaving a solid. The solid was triturated with Et$_2$O, filtered, washed with Et$_2$O, and dried giving 5.85 g of a white solid of sufficient purity for use in the following reaction. The structure was confirmed by NMR and mass spectroscopy.

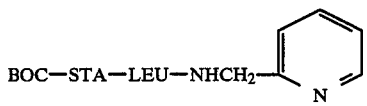

A solution of 1.84 g (6.05 mmole) BOC-STA and 0.86 g (6.35 mmole) HOBT in 20 ml DMF was cooled to −5°. A solution of 1.78 g (6.05 mmole)

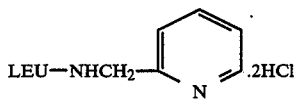

in 20 ml DMF and 1.8 ml (12.9 mmole) Et$_3$N was cooled to 0° and added to the previously described solution. To the combined solutions was added 1.31 g (6.35 mmole) DCC, and the solution stirred and allowed to warm to room temperature overnight. The mixture was filtered and the solvent removed under high vacuum. The residue was taken up in EtOAc and washed with 1N citric acid, saturated NaCl, saturated NaHCO$_3$, and saturated NaCl. After drying the solution was evaporated and the residue was chromatographed on silica gel, eluting with a gradient of 0 to 10% MeOH in CHCl$_3$. There was obtained 2.89 g of the product as a foam, of sufficient purity for use in the following reaction. The structure was confirmed by mass spectroscopy.

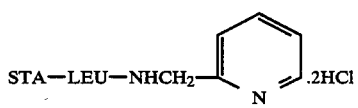

A solution of 2.2 g (4.46 mmole) of

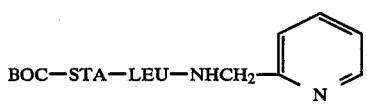

in 150 ml CH$_2$Cl$_2$ was occasionally purged with HCl gas over hours. The solution was evaporated ulcer reduced pressure and the residue was triturated with Et$_2$O. The solids were filtered, washed with Et$_2$O, and dried to give 2.05 g of a white solid, of sufficient purity for use in the following reaction. The structure was confirmed by NMR and mass spectroscopy.

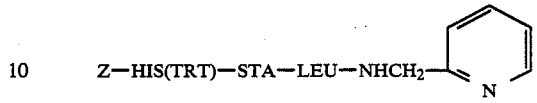

A solution of 2.32 g (4.36 mmole) of Z-HIS(TRT) and 0.62 g (4.59 mmole) of HOBT in 45 ml DMF was cooled to −5°. A solution of 1.99 g (4.36 mmole) of

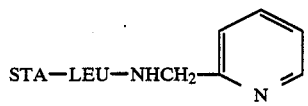

.2HCl and 1.28 ml (9.17 mmole) Et$_3$N in 30 ml DMF was cooled to −5° and added to the previously prepared solution. To the combined solutions, 0.90 g (4.59 mmole) DCC was added, and the mixture was allowed to warm to room temperature overnight. The mixture was filtered, and the solvent removed under high vacuum. The residue was taken up in EtOAc and washed with 1N citric acid, H$_2$O, saturated NaHCO$_3$, and saturated NaCl. After drying, the solution was evaporated and the residue was chromatographed on silica gel, eluting with a gradient of 0 to 10% MeOH in CHCl$_3$. There was obtained 3.41 g of product as a white foam, of sufficient purity for use in the following reaction. The structure was confirmed by mass spectroscopy.

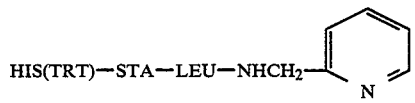

To a solution of 3.4 g (3.81 mmole) of

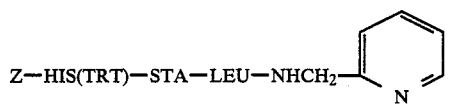

in 75 ml MeOH was added 0.35 g of 20% Pd/C catalyst, and the mixture purged with hydrogen. After five hours, the mixture was filtered, 0.37 g of 20% Pd/C catalyst added to the filtrate, and the mixture was again purged with hydrogen. After two hours, the mixture was filtered and the solvent removed under reduced pressure, giving a foam, 2.75 g, of sufficient purity for use in the following reaction. The structure was confirmed by mass spectroscopy.

A solution of 1.23 g (3.63 mmole) of di-(1-naphthylmethyl)acetic acid, 2.75 g (3.63 mmole) of

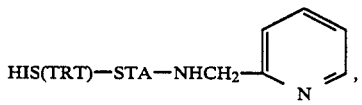

and 0.52 g (3.81 mmole) HOBT in 100 ml DMF was cooled to −5°. 0.79 g (3.81 mmole) DCC was added and the mixture was stored overnight at 4°. The solvent was removed under high vacuum and the residue was taken up in EtOAc. The suspension was filtered, and the filtrate was washed with 1N citric acid, saturated NaCl, saturated NaHCO$_3$, and saturated NaCl. After drying, the solvent was removed under reduced pressure, and the residue was chromatographed on silica gel, eluting with a gradient of 0 to 5% MeOH in CHCl$_3$. There was obtained 2.06 g of product as a white foam, of sufficient purity for use in the following reaction. The structure was confirmed by mass spectroscopy.

INTERMEDIATES FOR EXAMPLE 14

BOC-(D-HIS)(TOS)-STA-LEU-NHCH$_2$Ph

A solution of 0.98 g (2.4 mmole) of BOC-(D-HIS)-(TOS) in 100 ml CH$_2$Cl$_2$ was cooled in ice and 0.5 g (2.4 mmole) of DCC added. After five minutes STA-LEU-NHCH$_2$Ph [prepared by neutralizing 1.0 g (2.4 mmole) of STA-LEU-NHCH$_2$Ph.HCl with 0.24 g (2.4 mmole) of Et$_3$N] was added and the mixture kept at 4° for sixty-three hours. The mixture was then filtered and washed with saturated NaHCO$_3$, 1N citric acid, and saturated NaCl. Drying and removal of the solvent under reduced pressure gave the crude product. Chromatography on silica gel, eluting with CH$_2$Cl$_2$/MeOH (98/2) gave 1.4 g of the product, mp 97°–101°. The structure was confirmed by NMR and mass spectroscopy.

(D-HIS)(TOS)-STA-LEU-NHCH$_2$Ph

A solution of 0.95 g (1.24 mmole) of BOC-(D-HIS)-(TOS)-STA-LEU-NHCH$_2$Ph in 50 ml of TFA was allowed to stand at room temperature for fifteen minutes and the solvent was then removed under reduced pressure. The residue was taken up in CH$_2$Cl$_2$ and washed with saturated NaHCO$_3$, then saturated NaCl. Drying and removal of the solvent under reduced pressure gave 0.94 g of the product.

DNMA-(D-HIS)(TOS)-STA-LEU-NHCH$_2$Ph

A solution of 0.422 g (1.24 mmole) of di-(1-naphthylmethyl)acetic acid in 200 ml of CH$_2$Cl$_2$ was cooled in ice and 0.26 g (1.24 mmole) of DCC added. After five minutes 0.94 g (1.24 mmole) of (D-HIS)(TOS)-STA-LEU-NHCH$_2$Ph was added and the mixture kept at 4° for fifteen hours. The mixture was filtered and the filtrate was extracted with saturated NaHCO$_3$, then saturated NaCl. Drying and removal of the solid under reduced pressure gave the crude product. Chromatography on silica gel, eluting with CH$_2$Cl$_2$/MeOH (98/2) gave 0.95 g of product, mp 113°–116°. The structure was confirmed by NMR and mass spectroscopy.

BOC-(D-LEU)-NHCH$_2$Ph

A solution of 10.0 g (0.04 mmole) of BOC-(D-LEU) and 6.13 g (0.04 mmole) of HOBT in 200 ml DMF was cooled in ice and 8.3 g (0.04 mmole) of DCC in 40 ml DMF added, followed by 4.3 g (0.04 mmole) of benzylamine. The mixture was kept at 0° for two hours, then at 4° for fifteen hours. The mixture was filtered and the solvent removed under high vacuum. The residue was taken up in EtOAc, filtered, and extracted with 1N HCl, saturated NaHCO$_3$, and saturated NaCl. Drying and removal of the solvent under reduced pressure gave the crude product which was recrystallized from hexane to give 11.4 g of pure product, mp 85°–87°. The structure was confirmed by NMR and mass spectroscopy.

BOC-STA-(D-LEU)-NHCH$_2$Ph

A solution of 3.0 g (9.4 mmole) of BOC-(D-LEU)-NHCH$_2$Ph in 20 ml TFA was allowed to stand at room temperature for fifteen minutes and was then evaporated under reduced pressure. The residue was taken up in 100 ml CH$_2$Cl$_2$, cooled, and neutralized with 0.95 g (9.4 mmole) of Et$_3$N. To this was added a cold solution of 2.6 g (9.4 mmole) of BOC-STA, 1.44 g (9.4 mmole) of HOBT, and 1.94 g (9.4 mmole) of DCC in 150 ml of DMF. The mixture was kept at 4° for 15 hours, filtered, and evaporated under high vacuum. The residue was taken up in EtOAc and washed with 1N HCl, saturated Na$_2$CO$_3$, and saturated NaCl. Drying and removal of the solvent under reduced pressure gave a white solid. Chromatography on silica gel, eluting with CH$_2$Cl$_2$/MeOH (98/2) gave 3.31 g of product, mp 129°–130.5°. The structure was confirmed by NMR and mass spectroscopy.

STA-(D-LEU)-NHCH$_2$Ph.HCl

A solution of 2.37 g (4.96 mmole) of BOC-STA-(D-LEU)-NHCH$_2$Ph in 100 ml of CH$_2$Cl$_2$ was treated with 300 ml CH$_2$Cl$_2$ saturated with HCl gas. After standing for two and one-half hours at room temperature, the solution was evaporated under reduced pressure giving a white solid. The solid was suspended in Et$_2$O and evaporated under reduced pressure to give 2.17 g of the product, mp 100°–104°. The structure was confirmed by NMR and mass spectroscopy.

BOC-HIS(TOS)-STA-(D-LEU)-NHCH$_2$Ph

A solution of 2.0 g (4.96 mmole) of BOC-HIS(TOS) in 200 ml CH$_2$Cl$_2$ was cooled in ice and 1.0 g (4.96 mmole) of DCC added. After five minutes a solution of STA-(D-LEU)-NHCH$_2$Ph [prepared by neutralizing 2.0 g (4.96 mmole) of STA-(D-LEU)-NHCH$_2$Ph.HCl with 0.5 g (4.96 mmole) of Et$_3$N] in 100 ml CH$_2$Cl$_2$ was added and the mixture kept at 4° for fifteen hours. The mixture was filtered and washed with saturated NaHCO$_3$, 1N citric acid, and saturated NaCl. Drying and removal of the solvent under reduced pressure gave an oil. Chromatography on silica gel, eluting with CH$_2$Cl$_2$/MeOH (98/2) gave 1.0 g of product, mp 102°–105°. The structure was confirmed by NMR and mass spectroscopy.

HIS(TOS)-STA-(D-LEU)-NHCH$_2$Ph

A solution of 1.3 g (1.69 mmole) of BOC-HIS(TOS)-STA-(D-LEU)-NHCH$_2$Ph in 50 ml TFA was allowed to stand at room temperature for twenty minutes and was then evaporated under reduced pressure to an oil. The oil was taken up in CH$_2$Cl$_2$ and washed with saturated NaHCO$_3$ and saturated NaCl. Drying and removal of the solvent in vacuo gave 1.2 g of the product as a semi-solid. The material was sufficiently pure to use in the following step.

DNMA-HIS(TOS)-STA-(D-LEU)-NHCH₂Ph

A solution of 0.575 g (1.69 mmole) of di-(1-naphthylmethyl)acetic acid in 100 ml of CH₂Cl₂ was cooled in ice and 0.35 g (1.69 mmole) of DCC added. After five minutes 1.13 g (1.69 mmole) of HIS(TOS)-STA-(D-LEU)-NHCH₂Ph was added and the mixture kept at 4° for sixty hours. The mixture was filtered and the filtrate washed with saturated NaHCO₃ and saturated NaCl. Drying and removal of the solvent under reduced pressure left the crude product. Chromatography on silica gel, eluting with CH₂Cl₂/MeOH (98/2) gave 0.8 g of the product, mp 153°–156°. The structure was confirmed by NMR and mass spectroscopy.

INTERMEDIATES FOR EXAMPLES 16–18

BOC-CYSTA-LEU-NHCH₂Ph

A solution of 8.0 g (25.4 mmole) of BOC-CYSTA, 6.7 g (25.4 mmole) of LEU-NHCH₂Ph.HCl, and 3.43 g (25.4 mmole) of HOBT in 100 ml DMF was cooled in ice and treated with 3.6 ml (25.4 mmole) of Et₃N followed by 5.29 g (25.4 mmole) of DCC in 10 ml of DMF. After stirring at 0° for one-half hour, the mixture was allowed to stir at room temperature overnight.

The urea was filtered off and the solvent removed under high vacuum at 40°. The residue was taken up in EtOAc, filtered, and washed with 1N HCl, H₂O, saturated NaHCO₃, then saturated NaCl. After removal of the solvent under reduced pressure, the residue was chromatographed on 520 g of silica gel, eluting with CHCl₃/MeOH (98/2). Combining the appropriate fractions gave 13.1 g of product, suitable for use in the following reaction. The structure was confirmed by mass spectroscopy.

CYSTA-LEU-NHCH₂Ph.HCl

A solution of 13.1 g (25.3 mmole) of BOC-CYSTA-LEU-NHCH₂Ph in 100 ml of CH₂Cl₂ was treated with HCl gas for one hour. The solvent was removed under reduced pressure, the residue taken up in CH₂Cl₂ and the solvent again removed under reduced pressure leaving 8.2 g of a foam. Mass spectra confirmed the structure.

Calcd. for $C_{24}H_{39}N_3O_3 \cdot HCl \cdot 0.2H_2O$ (MW 457.64): C, 62.98; H, 8.90; N, 9.18: Found C, 62.92; H, 8.83; N, 9.14.

BOC-ASP(OCH₂Ph)-CYSTA-LEU-NHCH₂Ph

A solution of 5.0 g (10.9 mmole) of CYSTA-LEU-NHCH₂Ph.HCl, 3.54 g (10.9 mmole) of BOC-β-benzylaspartic acid, and 1.48 g (10.9 mmole) of HOBT in 50 ml of DMF was cooled in ice and treated with 1.53 ml (10.9 mmole) of Et₃N followed by 2.28 g (10.9 mmole) of DCC in 10 ml DMF. After stirring for one hour at 0°, the mixture was allowed to stir at room temperature overnight.

The urea was filtered off and the DMF removed under high vacuum. The residue was taken up in EtOAc, filtered, and washed with 1N HCl, H₂O, saturated NaHCO₃, then saturated NaCl. Drying and removal of the solvent under reduced pressure left 7.8 g of the product of sufficient purity to use in subsequent reactions. The structure was confirmed by mass spectroscopy.

ASP(OCH₂Ph)-CYSTA-LEU-NHCH₂Ph

A solution of 7.8 g (10.8 mmole) of BOC-ASP(OCH₂Ph)-CYSTA-LEU-NHCH₂Ph in 75 ml of CH₂Cl₂ was treated with 50 ml of TFA and stirred at room temperature for one hour. The solvent was removed under reduced pressure, CH₂Cl₂ added, and the solvent removed again under reduced pressure. The residue was taken up in EtOAc, washed twice with saturated NaHCO₃, then with saturated NaCl. Drying and removal of the solvent under reduced pressure left 6.7 g of the product as a foam. The structure was confirmed by mass spectroscopy.

INTERMEDIATES FOR EXAMPLE 19

Z-HIS(TRT)-CYSTA-LEU-NHCH₂Ph

To a solution of 1.59 g (3.0 mmole) of Z-HIS(TRT), 1.36 g (3.0 mmole) of CYSTA-LEU-NHCH₂Ph.HCl, 0.44 ml (3.15 mmole) of Et₃N and 426 mg (3.15 mmole) of HOBT in 30 ml of DMF at 0° was added 650 mg (3.15 mmole) of DCC. The mixture was allowed to warm to room temperature overnight. The urea was filtered off and the filtrate concentrated and diluted with EtOAc. The organic layer was washed with saturated NaHCO₃, H₂O, and brine. Drying over MgSO₄ and concentrating under reduced pressure left the crude product. Chromatography on silica gel, eluting with a gradient of 0–2% MeOH in CHCl₃ gave 1.9 g of product. The structure was confirmed by NMR spectroscopy.

HIS(TRT)-CYSTA-LEU-NHCH₂Ph

A solution of 1.68 g (1.81 mmole) of Z-HIS(TRT)-CYSTA-LEU-NHCH₂Ph in 200 ml of MeOH was treated with 170 mg of 20% Pd/C and stirred under an atmosphere of hydrogen for ten hours. The mixture was filtered and the solvent removed under reduced pressure. The residue was taken up in CHCl₃, washed with H₂O, dried, and concentrated to give 1.22 g of product. The structure was confirmed by NMR spectroscopy.

DNMA-HIS(TRT)-CYSTA-LEU-NHCH₂Ph

To a solution of 1.16 g (1.46 mmole) of HIS(TRT)-CYSTA-LEU-NHCH₂Ph, 495 mg (1.46 mmole) of di-(1-naphthylmethyl)acetic acid, and 207 mg (1.53 mmole) of HOBT in 15 ml of DMF at 0° was added 316 mg (1.53 mmole) of DCC. The mixture was allowed to warm to room temperature overnight. The urea was filtered off and the filtrate concentrated, diluted with EtOAc, and washed twice with saturated NaHCO₃. Drying over MgSO₄ and concentrating under reduced pressure afforded the crude product. Chromatography on silica gel, eluting with a gradient of a 0–2% MeOH in CHCl₃ gave 1.6 g of the product. The structure was confirmed by NMR spectroscopy.

INTERMEDIATES FOR EXAMPLE 20

BOC-(N-MeHIS)(TOS)-STA-LEU-NHCH₂Ph

To a solution of 1.27 g (3.0 mmole) of BOC-(N-MeHIS)(TOS) (J. Med. Chem. 1986. 29, 2088), 1.13 g (3.0 mmole) of STA-LEU-NHCH₂Ph and 0.46 ml (3.30 mmole) of Et₃N in 30 ml of CH₂Cl₂ at 0° was added 0.50 ml (3.30 mmole) of diethylcyanophosphonate. The solution was stirred and allowed to warm to room temperature overnight. It was then diluted with CH₂Cl₂, washed with saturated NaHCO₃, dried, and concentrated under reduced pressure to afford the crude product. Chromatography on silica gel, eluting with a gradient of 0–2% MeOH in CHCl₃ gave 1.2 g of product. The structure was confirmed by NMR spectroscopy.

(N-MeHIS)(TOS)-STA-LEU-NHCH2Ph

To a solution of 1.75 g (2.24 mmole) of BOC-(N-MeHIS)(TOS)-STA-LEU-NHCH2Ph in 30 ml of CH2Cl2 was added 30 ml of TFA. The solution was stirred at room temperature for one hour and concentrated at reduced pressure. The residue was diluted with CHCl3, washed with saturated NaHCO3, dried and concentrated under reduced pressure to afford 1.53 g of the product. The structure was confirmed by NMR spectroscopy.

DNMA-(N-MeHIS)(TOS)-STA-LEU-NHCH2Ph

To a solution of 1.68 g (2.46 mmole) of (N-MeHIS)-(TOS)-STA-LEU-NHCH2Ph, 837 mg (2.46 mmole) of di-(1-naphthylmethyl) acetic acid, and 0.38 ml (2.71 mmole) of Et3N in 25 ml of CH2Cl2 at 0° was added 0.41 ml (2.71 mmole) of diethylcyanophosphonate. The solution was stirred for eighteen hours at room temperature. It was then diluted with CH2Cl2, washed with saturated NaHCO3, dried, and concentrated under reduced pressure to afford the crude product. Chromatography on silica gel, eluting with a gradient of 0-2% MeOH in CHCl3 afforded the product. The structure was confirmed by NMR spectroscopy.

INTERMEDIATES FOR EXAMPLE 21

Z-(N-MeLEU)-NHCH2Ph

To a solution of 4.0 g (14.3 mmole) of Z-(N-MeLEU) (Can. J. Chem. 1973, 51, 1915) in 50 ml of CH3CN was added 3.1 g (15.1 mmole) of DCC followed by 2.03 g (15.1 mmole) of HOBT. The mixture was stirred for fifteen minutes at room temperature and 1.64 ml (15.1 mmole) of benzylamine was added. The mixture was stirred for an additional fifteen hours at room temperature, filtered, concentrated under reduced pressure and diluted with EtOAc. The organic solution was washed with saturated NaHCO3, dried, and concentrated to an oil. Chromatography on silica gel, eluting with hexane/EtOAc (80/20) afforded 4.60 g of product. The structure was confirmed by NMR spectroscopy.

(N-MeLEU)-NHCH2Ph

To a solution of 4.6 g (12.5 mmole) of Z-(N-MeLEU)-NHCH2Ph in 200 ml of MeOH was added 460 mg of 20% Pd/C. The mixture was stirred under a hydrogen atmosphere at room temperature for twelve hours, filtered, and the solvent removed under reduced pressure. The residue was diluted with CH2Cl2, washed with saturated NaHCO3, dried, and concentrated under reduced pressure to afford 2.60 g of the product. The structure was confirmed by NMR spectroscopy.

BOC-STA-(N-MeLEU)-NHCH2Ph

To a solution of 2.22 g (8.08 mmole) of BOC-STA, 1.89 g (8.08 mmole) of (N-MeLEU)-NHCH2Ph and 1.15 g (8.48 mmole) of HOBT in 50 ml of CH3CN at 0° was added 1.75 g (8.48 mmole) of DCC. The mixture was stirred and allowed to warm to room temperature over a fifteen hour period. The urea was filtered off and the filtrate was concentrated under reduced pressure and diluted with EtOAc. The organic layer was washed with saturated NaHCO3, dried, and concentrated under reduced pressure to afford the crude product. Chromatography on silica gel, eluting with hexane/EtOAc (50/50) afforded 3.20 g of the product. The structure was confirmed by NMR spectroscopy.

STA-(N-MeLEU)-NHCH2Ph

To a solution of 3.2 g (6.52 mmole) of BOC-STA-(N-MeLEU)-NHCH2Ph in 50 ml of CH2Cl2 was added 50 ml of TFA. The solution was stirred for one hour and was concentrated under reduced pressure. The residue was diluted with CHCl3, washed with saturated NaHCO3, dried, and concentrated under reduced pressure to afford 2.44 g of the product. The structure was confirmed by NMR spectroscopy.

Z-HIS(TRT)-STA-(N-MeLEU)-NHCH2Ph

To a solution of 3.31 g (6.24 mmole) of Z-HIS(TRT), 2.44 g (6.24 mmole) of STA-(N-MeLEU)-NHCH2Ph and 880 mg (6.55 mmole) of HOBT in 60 ml of DMF at 0° was added 1.35 g (6.55 mmole) of DCC. The mixture was stirred and allowed to warm to room temperature overnight. The mixture was filtered and the filtrate was concentrated under reduced pressure and diluted with EtOAc. The organic layer was washed with saturated NaHCO3, dried, and concentrated under reduced pressure. The residue was chromatographed on silica gel, eluting with a gradient of 0-2% MeOH in CHCl3 to afford the product. The structure was confirmed by NMR spectroscopy.

HIS(TRT)-STA-(N-MeLEU)-NHCH2Ph

To a solution of 2.85 g (3.15 mmole) of Z-HIS(TRT)-STA-(N-MeLEU)-NHCH2Ph in 200 ml MeOH was added 300 mg of 20% Pd/C. The mixture was stirred under an atmosphere of hydrogen at room temperature for ten hours. The mixture was filtered and the solvent evaporated under reduced pressure to afford 2.43 g of the product. The structure was confirmed by NMR spectroscopy.

DNMA-HIS(TRT)-STA-(N-MeLEU)-NHCH2Ph

To a solution of 1.18 g (3.47 mmole) of di-(1-naphthylmethyl)acetic acid, 2.43 g (3.16 mmole) of HIS(TRT)-STA-(N-MeLEU)-NHCH2Ph and 469 mg (3.47 mmole) of HOBT in 25 ml of DMF at 0° was added 716 mg (3.47 mmole) of DCC. The mixture was stirred and allowed to warm to room temperature over a fifteen hour period. It was then filtered and the filtrate was concentrated under reduced pressure and diluted with EtOAc. The organic layer was washed twice with saturated NaHCO3, dried, and concentrated under reduced pressure to afford the crude product. Chromatography on silica gel, eluting with a gradient of 0-2% MeOH in CHCl3 gave 2.80 g of the product. The structure was confirmed by NMR spectroscopy.

INTERMEDIATE FOR EXAMPLES 22 AND 23

To a cold solution of 1.63 g (1.86 mmole) of DNMA-HIS(TRT)-STA, 260 mg (1.95 mmole) of HOBT, and 0.5 g (1.86 mmole) of

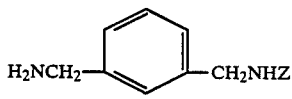

in 50 ml DMF was added 0.4 g (1.95 mmole) of DCC and the solution stirred at room temperature overnight. The mixture was then filtered and the solvent removed under high vacuum. The residue was taken up in EtOAc and washed with 1N citric acid, saturated NaCl, saturated NaHCO$_3$, and saturated NaCl. Drying and removal of the solvent under reduced pressure gave the crude product. Chromatography on silica gel, eluting with a gradient of 0–5% MeOH in CHCl$_3$ gave 1.87 g of the product as a white foam.

INTERMEDIATES FOR EXAMPLE 24

BOC-STA-NHCH$_2$CH=CH$_2$

To a solution of 27.5 g (100 mmole) BOC-STA and 14.2 g (105 mmole) HOBT in 40 ml DMF was added 350 ml CH$_2$Cl$_2$ followed by cooling to −5°. 7.5 ml (100 mmole) allylamine, and 21.7 g (105 mmole) DCC were added, and the mixture was allowed to warm to room temperature overnight. The mixture was filtered, and the solvent removed under high vacuum and the residue was taken up in EtOAc. The solution was washed with saturated NaCl, saturated NaHCO$_3$, saturated NaCl, 1N citric acid, and saturated NaCl. After drying, the solution was evaporated to one-half volume and the product was isolated by addition of hexane to the solution, giving a crystalline solid, 28.9 g. The structure was confirmed by NMR and mass spectroscopy.

STA-NHCH$_2$CH=CH$_2$

To a solution of 28.6 g (91 mmole) of BOC-STA-NHCH$_2$CH=CH$_2$ in 100 ml CH$_2$Cl$_2$ was added 125 ml TFA and the solution stirred at room temperature for six hours. The solvent was removed under reduced pressure and the residue taken up in EtOAc and washed with saturated NaCl which had been adjusted to pH 12 with 5N NaOH, then with saturated NaCl. Drying and removal of the solvent under reduced pressure gave 21.07 g of the product as an oil of sufficient purity for use in the following reaction.

BOC-HIS-STA-NHCH$_2$CH=CH$_2$

A solution of 23.23 g (0.091 mole) of BOC-HIS, 12.9 g (0.095 mole) of HOBT, and 19.5 g (0.091 mole) of STA-NHCH$_2$CH=CH$_2$ in 300 ml DMF was cooled in ice and 19.7 g (0.095 mole) of DCC added. The solution was then allowed to warm to room temperature overnight. The mixture was filtered and the solvent removed under high vacuum. The residue was taken up in EtOAc and washed with 1N citric acid. The citric acid wash was made basic with sodium carbonate solution and extracted with EtOAc. The EtOAc was washed with saturated NaCl, dried, and concentrated under reduced pressure. The concentrate was poured into excess Et$_2$O precipitating 26.5 g of a white solid. Since thin layer suggested the presence of appreciable material acylated on the imidazole portion of the product by additional BOC-HIS, the 26.5 g was dissolved in 250 ml MeOH and treated with 2.8 g of 50% NaOH. The solution was stirred for two hours at room temperature, the pH adjusted to 7.0 with dilute HCl, and the solvent removed under reduced pressure. The residue was taken up in CHCl$_3$ and washed with saturated NaHCO$_3$ and saturated NaCl. After drying the solution was concentrated under reduced pressure and poured into excess Et$_2$O. The precipitate was collected to give 17.6 g of product. The structure was confirmed by NMR and mass spectroscopy.

HIS-STA-NHCH$_2$CH=CH$_2$

A solution of 12.5 g (27.7 mmole) of BOC-HIS-STA-NHCH$_2$CH=CH$_2$ in 50 ml CH$_2$Cl$_2$ was treated with 50 ml TFA and stirred at room temperature for one hour. The solvent was then removed under reduced pressure and the residue mixed with H$_2$O and the pH adjusted to 13 with 5N NaOH. This was extracted with EtOAc, then CHCl$_3$. The organic phases were combined and washed with saturated NaCl, dried, and the solvent removed under reduced pressure. The residue was taken up in EtOAc and precipitated by adding to excess Et$_2$O. Since the solid still contained sodium trifluoroacetate, it was taken up in H$_2$O and repeatedly extracted with EtOAc. The EtOAc extracts were dried and the solvent removed under reduced pressure giving 7.08 g of product, sufficiently pure for use in the next reaction.

We claim:
1. A peptide of the formula

ACYL—X—Y—W—U    (I)

and the pharmaceutically acceptable acid addition salts thereof, wherein ACYL is DNMA,

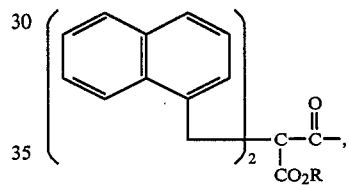

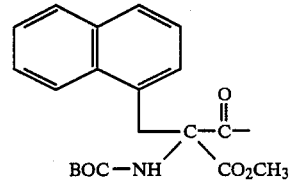

wherein R is hydrogen or a straight or branched lower alkyl of from one to six carbon atoms,

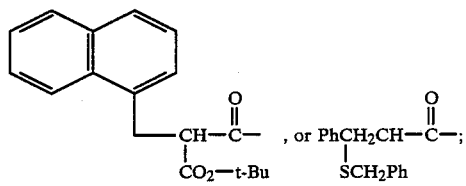

X is HIS, HOMOHIS, PHE, HOMOPHE, ILE, LEU, NLE, N-MeHIS, N-MeLEU, or

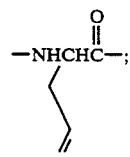

Y is STA, CYSTA, or PHSTA;
W is LEU, ILE, N-MeLEU, N-MeILE, VAL or absent with the proviso that, when ACYL is DNMA, W is present; and
U is —NHCH$_2$CH(CH$_3$)CH$_2$CH$_3$, —NHCH$_2$Ph,

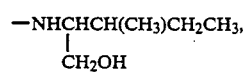

—NHCH$_2$CH(OH)CH$_2$SCH(CH$_3$)$_2$, —NHCH$_2$CH(OH)CH$_2$SOCH(CH$_3$)$_2$, —NHCH$_2$CH(OH)CH$_2$SO$_2$CH(CH$_3$)$_2$,

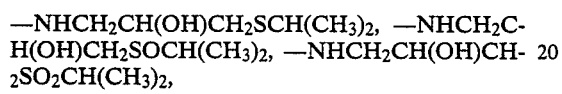

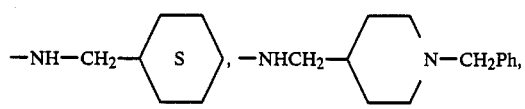

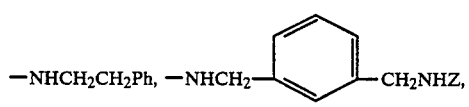

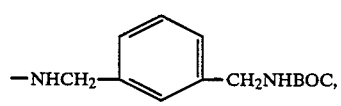

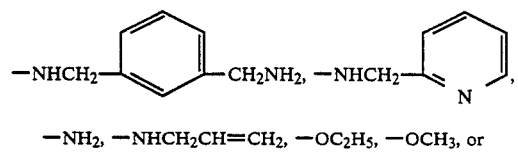

—NH$_2$, —NHCH$_2$CH=CH$_2$, —OC$_2$H$_5$, —OCH$_3$, or

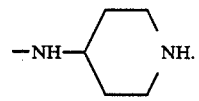

2. A peptide according to claim 1 wherein U is —NHCH$_2$Ph,

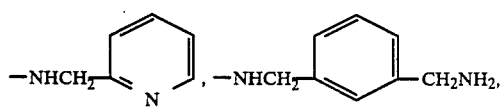

—NHCH$_2$CH=CH$_2$, —NHCH$_2$CH(OH)CH$_2$SCH(CH$_3$)$_2$, —NHCH$_2$CH(OH)CH$_2$SOCH(CH$_3$)$_2$, —NHCH$_2$CH(OH)CH$_2$SO$_2$CH(CH$_3$)$_2$,

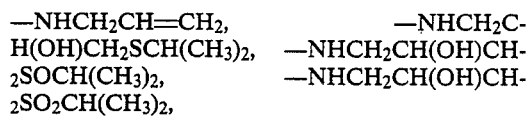

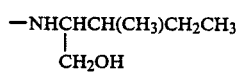

or —NHCH$_2$CH(CH$_3$)CH$_2$CH$_3$.

3. A peptide according to claim 1 wherein the peptide is a member selected from the group consisting of: and DNMA-HIS-STA-LEU-NHCH$_2$Ph,

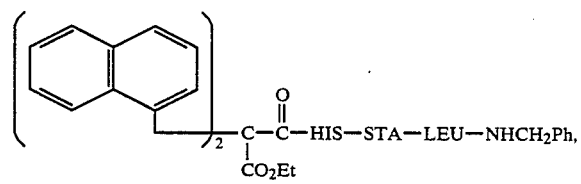

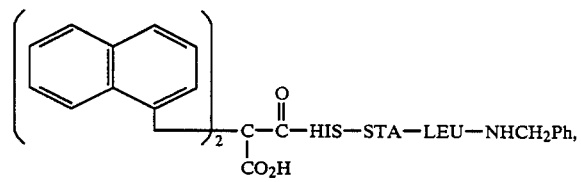

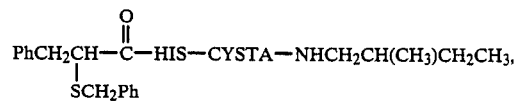

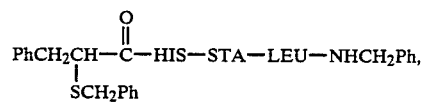

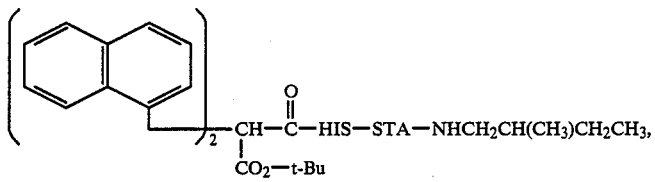

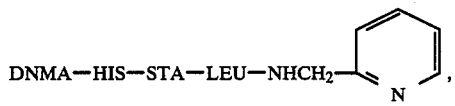

DNMA-(D-HIS)-STA-LEU-NHCH₂Ph,
DNMA-HIS-STA-(D-LEU)-NHCH₂Ph,
DNMA-(N-MeHIS)-STA-LEU-NHCH₂Ph,
DNMA-HIS-STA-(N-MeLEU)-NHCH₂Ph,
DNMA-HIS-CYSTA-LEU-NHCH₂Ph,

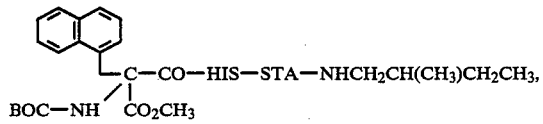

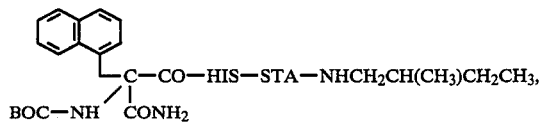

4. A compound named DNMA-HIS-STA-NHCH₂CH(OH)CH₂SO₂CH(CH₃)₂.

5. A pharmaceutical composition comprising a renin-inhibitory effective amount of a compound as claimed in claim 4 together with a pharmaceutically acceptable carrier.

6. A method of treating renin-associated hypertension which comprises administering to a mammal a pharmaceutical composition comprising a renin inhibitory effective amount of a compound as in claim 1 together with a pharmaceutically acceptable carrier.

7. A method of treating renin-associated hypertension which comprises administering to a mammal a pharmaceutical composition as claimed in claim 5.

8. A method of treating hyperaldosteronism which comprises administering to a mammal a pharmaceutical composition comprising an hyperaldosteronism-inhibitory effective amount of a compound as claimed in claim 1 together with a pharmaceutically acceptable carrier.

9. A method of determining the presence of renin-associated hypertension in a patient which comprises administering to said patient, at a hypotensive dosage level and as a single dose, a peptide of claim 1, followed by monitoring of said patient's blood pressure.

10. A method of treating congestive heart failure which comprises administering to a mammal a pharmaceutical composition comprising an amount effective for treating congestive heart failure of a compound as claimed in claim 1 together with a pharmaceutically acceptable carrier.

* * * * *